US008084413B2

(12) United States Patent
Vale, Jr. et al.

(10) Patent No.: US 8,084,413 B2
(45) Date of Patent: Dec. 27, 2011

(54) UROCORTIN-III AND USES THEREOF

(75) Inventors: Wylie W. Vale, Jr., La Jolla, CA (US); Kathy A. Lewis, San Diego, CA (US); Marilyn H. Perrin, La Jolla, CA (US); Koichi S. Kunitake, San Diego, CA (US); Jean E. Rivier, La Jolla, CA (US); Jozsef Gulyas, Julian, CA (US)

(73) Assignee: Research Development Foundation, Carson City, NV (US)

( * ) Notice: Subject to any disclaimer, the term of this patent is extended or adjusted under 35 U.S.C. 154(b) by 62 days.

(21) Appl. No.: 12/266,430

(22) Filed: Nov. 6, 2008

(65) Prior Publication Data

US 2009/0156493 A1 Jun. 18, 2009

Related U.S. Application Data

(60) Continuation of application No. 11/214,371, filed on Aug. 29, 2005, now Pat. No. 7,459,427, which is a continuation of application No. 10/771,224, filed on Feb. 3, 2004, now Pat. No. 6,953,838, which is a division of application No. 10/099,766, filed on Mar. 15, 2002, now Pat. No. 6,812,210.

(60) Provisional application No. 60/276,069, filed on Mar. 15, 2001, provisional application No. 60/294,914, filed on May 31, 2001.

(51) Int. Cl.
*C07K 14/00* (2006.01)
(52) U.S. Cl. .................... 514/1; 530/300; 530/350
(58) Field of Classification Search .................. 530/350, 530/300; 514/1
See application file for complete search history.

(56) References Cited

U.S. PATENT DOCUMENTS

| 5,869,450 | A | 2/1999 | Wei et al. ................ 514/12 |
| 5,959,109 | A | 9/1999 | Whitten et al. ............ 544/311 |
| 6,147,275 | A | 11/2000 | Vale et al. ................ 800/18 |
| 6,353,152 | B1 | 3/2002 | Lee et al. ................ 800/18 |
| 6,812,210 | B2 | 11/2004 | Vale et al. ................ 514/12 |
| 6,838,252 | B2 | 1/2005 | Vale, Jr. et al. .......... 435/252.3 |
| 6,953,838 | B2 | 10/2005 | Vale et al. ................ 435/6 |
| 7,291,341 | B2 | 11/2007 | Hsu et al. ................ 514/12 |
| 2002/0082409 | A1 | 6/2002 | Hsu et al. ................ 536/23.5 |
| 2004/0034882 | A1 | 2/2004 | Vale et al. ................ 800/18 |

FOREIGN PATENT DOCUMENTS

| WO | WO 97/00063 | 1/1997 |
| WO | WO 99/51261 | 10/1999 |
| WO | WO 02/34934 | 5/2002 |

OTHER PUBLICATIONS

U.S. Appl. No. 09/714,692, filed Nov. 16, 2000, Lee and Mar.
Brar et al., "Urocortin-II and urocortin-III are cardioprotective against ischemia reperfusion injury: an essential endogenous cardioprotective role for corticotropin releasing factor receptor type 2 in the murine heart," *Endocrinology*, 145:24-35, 2004.
Brunner et al., "Molecular cloning and characterization of the Fugu rubripes MEST/COPG2 imprinting cluster and chromosomal localization in Fugu and Tetradon nigroviridis," *Chromosome Research*, 8(6):465-476, 2000.
Chen et al., "Design and synthesis of a series of non-peptide high-affinity human corticotrophin-releasing factor 1 receptor antagonists," *J. Med. Chem.*, 39:4358-4360, 1996.
Christos et al., "Corticotropin-releasing factor receptor antagonists," *Expert Opinion on Therapeutic Patents*, 8(2):143-152, 1998.
Eckart et al., "Actiosn of CRF and its analogs," *Current Medicinal Chemsitry*, 6:1035-1053, 1999.
Hsu et al., "Human stresscopin and stresscopin-related peptide are selective ligands for the type 2 corticotropin-releasing hormone receptor," *Nature Medicine*, 7(5):605-611, 2001.
Lewis et al., "Identification of urocortin III, an additional member of the corticotropin-releasing factor (CRF) family with high affinity for the CRF2 receptor," *Proc. Natl. Acad Sci. USA*, 98:7570-7575, 2001.
Li et al., "Urocortin III-immunoreactive projections in rat brain: partial overlap with sites of type 2 corticotrophin-releasing factor receptor expression," *J. Neurosci.*, 22(3):991-1001, 2002.
Martinez et al., "Differential actions of peripheral corticotropin-releasing factor (CRF), urocortin II, and urocortin III on gastric emptying and colonic transit in mice: role of CRF receptor subtypes 1 and 2," *J. Pharmacology Exp. Thera.*, 301:611-617, 2002.
Martinez et al., "Urocortins and the regulation of gastrointestinal motor function and visceral pain," *Peptides*, 25:1733-1744, 2004.
National Cancer Institute, Cancer Genome Anatomy Project (NCI-CGAP), Genbank Accession No. AW293249, Jan. 16, 2000.
Office Communication issued in Canadian Application No. 2,425,902, dated May 23, 2008.
Office Communication issued in Israeli Application No. 154553, dated Feb. 24, 2008.
Office Communication issued in Japanese Patent Application No. 2002-573033, dated Feb. 19, 2008.
Office Communication, issued in U.S. Appl. No. 10/099,766, dated Apr. 8, 2004.
Office Communication, issued in U.S. Appl. No. 10/099,766, dated Nov. 5, 2003.

(Continued)

*Primary Examiner* — Karen Carlson
(74) *Attorney, Agent, or Firm* — Fulbright & Jaworski L.L.P.

(57) ABSTRACT

A search of the public human genome database identified a human EST, GenBank accession number AW293249, which has high homology to known pufferfish urocortin sequences. The full length sequence was amplified from human genomic DNA and sequenced. Sequence homology comparisons of the novel sequence with human urocortin I and urocortin II revealed that the sequence encoded a novel human urocortin, which was designated urocortin III (UcnIII). While urocortin III does not have high affinity for either CRF-R1 or CRF-R2, the affinity for CRF-R2 is greater than the affinity for CRF-R1. Urocortin III is capable stimulating cyclic AMP production in cells expressing CRF-R2α or β. Thus, the affinity is high enough that urocortin III could act as a native agonist of CRF-R2. However, it is also likely that urocortin III is a stronger agonist of a yet to be identified receptor.

14 Claims, 7 Drawing Sheets

OTHER PUBLICATIONS

Office Communication, issued in U.S. Appl. No. 10/771,224, dated Feb. 16, 2005.
Office Communication, issued in U.S. Appl. No. 11/214,371, dated Feb. 1, 2007.
Office Communication, issued in U.S. Appl. No. 11/214,371, dated Apr. 26, 2007.
Office Communication, issued in U.S. Appl. No. 11/214,371, dated Aug. 1, 2008.
Office Communication, issued in U.S. Appl. No. 11/214,371, dated Apr. 18, 2006.
Office Communication, issued in U.S. Appl. No. 11/214,371, dated Oct. 20, 2005.
Perrin et al., "A soluble form of the first extracellular domain of mouse type 2beta corticotropin-releasing factor receptor reveals differential ligand specificity," *J. Biol. Chem.*, 278:155595-15600, 2003.
Reyes et al., "Urocortin II: A member of the corticotropin-releasing factor (CRF) neuropeptide family that is selectively bound by type 2 CRF receptors," *PNAS*, 98(5):2843-2848, 2001.
Rühmann et al., "Structural requirements for peptidic antagonists of the corticotropin-releasing factor receptor (CRFR): Development of CRF2β-selective antisauvagine-30," *Proc. Natl. Sci. USA*, 95:15264-15269, 1998.
Schulz et al., "CP-154,526: A potent and selective non-peptide high-affinity antagonist of corticotrophin releasing factor receptors," *PNAS*, 93:10477-10482, 1996.
Skelton et al., "The neurobiology of urocortin," *Regulatory Peptides*, 93(1-3):85-92, 2000.
Supplementary European Search Report issued in European Application No. 02753685.3, dated Sep. 19, 2005.
Valdez et al., "Locomotor suppressive and anxiolytic-like effects of urocortin 3, a highly selective type 2 corticotropin-releasing factor agonist," *Brain Res.*, 80:206-212, 2003.
Office Communication, issued in Russian Patent Application No. 2007110981/10(011938), dated Dec. 27, 2011. (English translation).
Office Communication, issued in Canadian Patent Application No. 2,425,902, dated May 4, 2011.

aattcggcacgagggggaccgtttccatagagagggaatatcacagcccacttaggaac 59 aatacctggagaagcaggagccgagaccccggagcagccacaagttcatggggacgtgca 119 tggggccgccctcctggccctgaagctgcgccggcctccctgagcgtttcgctgcggagg 179 gaagtccactctcggggagagatgctgatgccggtccacttcctgctgctcctgctgctg 239
            M   L   M   P   V   H   F   L   L   L   L   L ctcctggggggccccaggacaggcctcccccacaagttctacaaagccaagcccatcttc 299
 L   L   G   G   P   R   T   G   L   P   H   K   F   Y   K   A   K   P   I   F agctgcctcaacaccgccctgtctgaggctgagaagggccagtgggaggatgcatccctg 359
 S   C   L   N   T   A   L   S   E   A   E   K   G   Q   W   E   D   A   S   L ctgagcaagaggagcttccactacctgcgcagcagagacgcctcttcgggagaggaggag 419
 L   S   K   R   S   F   H   Y   L   R   S   R   D   A   S   S   G   E   E   E gagggcaaagagaaaaagactttccccatctctggggccaggggtggagccggaggcacc 479
 E   G   K   E   K   K   T   F   P   I   S   G   A   R   G   G   A   G   G   T cgttacagatacgtgtcccaagcacagcccaggggaaagccacgccaggacacagccaag 539
 R   Y   R   Y   V   S   Q   A   Q   P   R   G   K   P   R   Q   D   T   A   K agtccccaccgcaccaagttcaccctgtccctcgacgtccccaccaacatcatgaacctc 599
 S   P   H   R   T   K   F   T   L   S   L   D   V   P   T   N   I   M   N   L ctcttcaacatcgccaaggccaagaacctgcgtgcccaggcggccgccaatgcccacctg 659
 L   F   N   I   A   K   A   K   N   L   R   A   Q   A   A   A   N   A   H   L atggcgcaaattgggaggaagaagtagagg  (SEQ ID NO.: 1)  689
 M   A   Q   I   G   R   K   K   *  (SEQ ID NO.: 2)

Fig. 1

MLMPVHFLLLLLLLLGGPRTGLPHKFYKAKPIFSCLNTALSEAEKGQWED 50
ASLLSKRSFHYLRSRDASSGEEEEGKEKKTFPISGARGGAGGTRYRYVSQ 100
AQPRGKPRQDTAKSPHRTK FTLSLDVPTNIMNLLFNIAKAKNLRAQAAAN 150
AHLMAQI GRKK 161

(SEQ ID NO.: 2)

Fig. 2A

MLMPTYFLLPLLLLLGGPRTSLSHKFYNTGPVFSCLNTALSEVKKNKLED 50
VPLLSKKSFGHLPTQDPSGEEDDNQTHLQIKRTFSGAAGGNGAGSTRYRY 100
QSQAQHKGKLYPDKPKSDRGTK FTLSLDVPTNIMNILFNIDKAKNLRAKA 150
AANAQLMAQI GKKK 164

(SEQ ID NO.: 4)

Fig. 2B

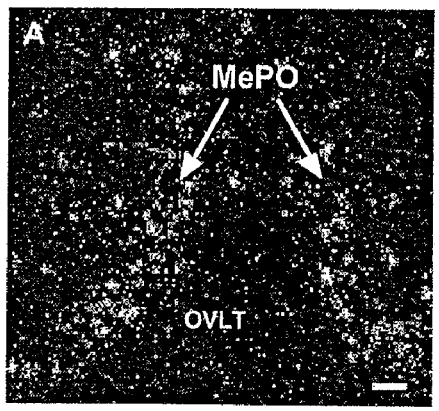
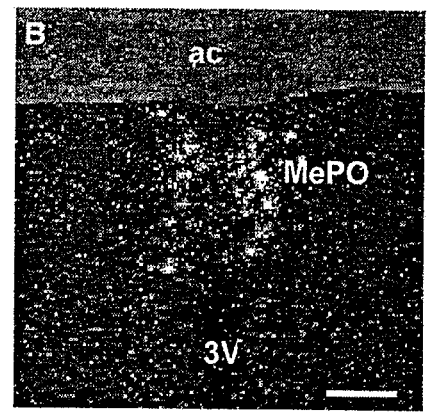
Fig. 5A
Fig. 5B
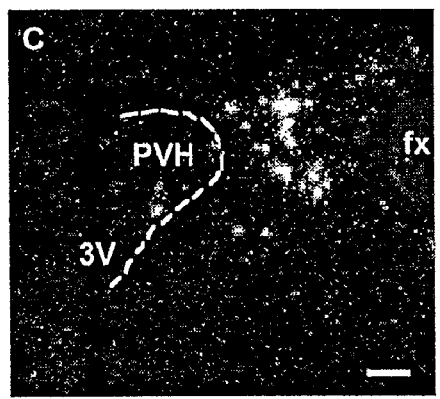
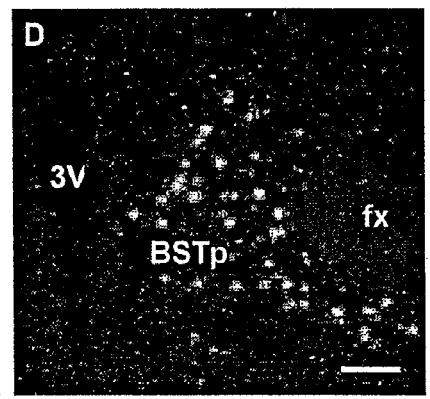
Fig. 5C
Fig. 5D
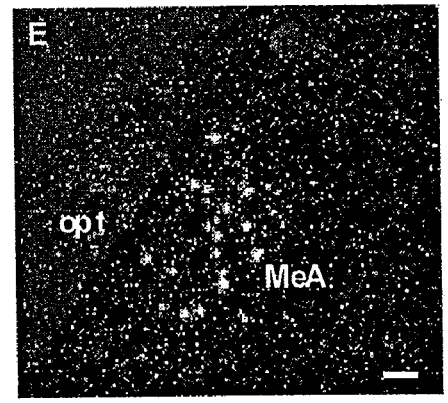
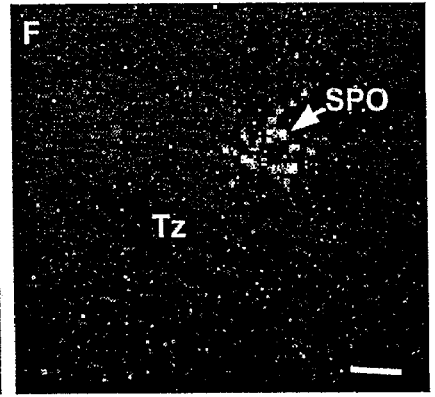
Fig. 5E
Fig. 5F

UROCORTIN-III AND USES THEREOF

CROSS-REFERENCE TO RELATED APPLICATION

This application is a continuation of application U.S. Ser. No. 11/214,371, filed Aug. 29, 2005, now U.S. Pat. No. 7,459,427, which is a continuation of U.S. application Ser. No. 10/771,224 filed on Feb. 3, 2004, now issued as U.S. Pat. No. 6,953,838, which is a divisional application of U.S. application Ser. No. 10/099,766 filed on Mar. 15, 2002, now issued as U.S. Pat. No. 6,812,210, which claims the benefit of U.S. Provisional Application No. 60/276,069, filed Mar. 15, 2001, and U.S. Provisional Application No. 60/294,914, filed May 31, 2001. The entire contents of each of the above referenced disclosures is incorporated herein by reference without disclaimer.

FEDERAL FUNDING LEGEND

This invention was produced in part using funds from the Federal government under grant no P01-DK-26741. Accordingly, the Federal government has certain rights in this invention.

BACKGROUND OF THE INVENTION

1. Field of the Invention

The present invention relates generally to the fields of neuroendocrinology and neuropeptide chemistry. More specifically, the instant invention relates to protein factors involved in the regulation of neuroendocrine and paracrine responses to stress. Most specifically, the present invention discloses a corticotropin releasing factor related peptide designated urocortin III.

2. Description of the Related Art

Corticotropin releasing factor (CRF) and its related family of peptides were recognized initially for their regulation of the hypothalamic-pituitary-adrenal axis (HPA) under basal and stress conditions (1, 2). Corticotropin releasing factor (CRF) is a 41 amino acid peptide that was first isolated from ovine hypothalamus (3) and shown to play an important role in the regulation of the pituitary-adrenal axis, and in endocrine, autonomic and behavioral responses to stress (4). The CRF family of neuropeptides also includes structurally related mammalian and non-mammalian peptides such as urocortin (Ucn), a 40 amino acid peptide originally identified in rat brain (5), fish urotensin I (Uro) (6), and amphibian sauvagine (Svg) (7).

It has been hypothesized that members of the CRF family are involved in neuroendocrine and paracrine responses in many tissues. In addition to their effects on the pituitary and central nervous system, members of the CRF family have been shown to modulate cardiovascular and gastrointestinal functions and inflammatory processes in mammals to integrate endocrine, autonomic and behavioral responses to stressors. These peptides may also be implicated in the control of appetite, arousal, and cognitive functions. Severe psychological and physiological consequences can occur as a result of the long term effects of stress, such as anxiety disorders, anorexia nervosa, gastrointestinal dysfunction and melancholic depression.

CRF family members mediate their biological actions by specifically binding to CRF receptors with high affinities (8, 9). CRF receptors are G-protein coupled receptors that act through adenylate cyclase and are structurally related to the secretin receptor family. This family also includes GRF, VIP, PTH, and the calcitonin receptors.

The CRF receptors are derived from two distinct genes, CRF receptor type 1 (CRF-R1) (10-12) and CRF receptor type 2 (CRF-R2) (13-15). CRF-R1 and CRF-R2 have distinct pharmacologies and differ in their anatomical distribution (16). The type 1 CRF receptor (CRF-R1) gene has 13 exons; several splice variants of this receptor have been found. The CRF-R1 is distributed throughout the brain and is found in sensory and motor relay sites (17). The rodent type 2α receptor (CRF-R2α) is distributed in lateral septum, ventral medial hypothalamus, nucleus of the solitary tract and the dorsal raphe nucleus, which are areas where CRF-R1 is expressed very little or not at all (18). The rodent type 2β receptor (CRF-R2β) is found mostly in peripheral sites including the heart, blood vessels, gastrointestinal tract, epididymis, lung and skin (9, 19).

The pharmacology of the two types of receptors differs in that CRF has a modest affinity for CRF-R2 [Ki=5-100 nM] but high affinity for CRF-R1 [Ki=1-2 nM]. Other related peptides such as carp urotensin, frog sauvagine, and urocortin have a high affinity for both CRF-R1 and CRF-R2. CRF-R2 knockout mice demonstrate an increased anxiety-like behavior caused by hypersensitivity to stressors (5, 20).

Recently, searches of the public human genome database identified a region with significant sequence homology to the CRF neuropeptide family. The entire human sequence was amplified and sequenced. The human sequence, however, lacks a consensus proteolytic cleavage site that would allow for C-terminal processing of the peptide, and is therefore referred to as an urocortin-related peptide (URP) sequence. Using homologous primers deduced from the human sequence, a mouse cDNA was isolated from whole brain poly (A+) RNA that encodes a predicted 38 amino acid peptide, designated urocortin II, which is structurally related to the other known mammalian family members, CRF and urocortin (Ucn). The question of whether human urocortin-related peptide represents the mouse Ucn II ortholog remains open until additional mouse genes are identified. Ucn II binds selectively to the type 2 CRF receptor (CRF-R2), with no appreciable activity on CRF-R1. Transcripts encoding Ucn II are expressed in discrete regions of the rodent CNS, including stress-related cell groups in the hypothalamus (paraventricular and arcuate nuclei) and brainstem (locus coeruleus). These findings identify Ucn II as a new member of the CRF family of neuropeptides, which is expressed centrally and binds selectively to CRF-R2. Initial functional studies are consistent with Ucn II involvement in central autonomic and appetitive control, but not in generalized behavioral activation (21).

The prior art is deficient in the recognition of the human Urocortin-III gene and protein and uses thereof. The present invention fulfills this longstanding need and desire in the art.

SUMMARY OF THE INVENTION

A human urocortin, Urocortin-III (Ucn-III) with homology to known pufferfish urocortins was identified from the public human genome database. From the sequence of the human gene, a mouse ortholog was isolated. The present invention relates to these novel genes and uses thereof.

In one aspect, the instant invention is directed to an isolated and purified urocortin III protein, which may be either mouse or human urocortin III. The mouse protein preferably has an amino acid sequence of SEQ ID NO:5, which is derived from a precursor peptide of SEQ ID NO:4. The human protein preferably has an amino acid sequence of SEQ ID No: 3 derived from a precursor peptide of SEQ ID NO:2.

The instant invention is also directed to human urocortin III containing one or more amino acid substitutions derived from the mouse amino acid sequence. The sequence of mouse urocortin III (SEQ ID NO:5) differs from human urocortin III (SEQ ID NO:3) by four amino acids, specifically $Ile_{14}$, $Asp_{19}$, $Lys_{27}$, and $Gln_{33}$. Substitution of the $Leu_{14}$ residue in the human protein with Ile is contemplated to be especially useful.

The instant invention is also directed to a pharmaceutical composition comprising a urocortin III protein and to a method of treating a pathophysiological state using this pharmaceutical composition. This pharmaceutical composition could be administered to activate the CRF-R2 receptor to remedy a pathophysiological state such as high body temperature, appetite dysfunction, congestive heart failure, vascular disease, stress and anxiety.

The instant invention is also directed to modification of a urocortin III protein. The N-terminus of urocortin III may be extended with additional amino acids or peptides such as Threonine-Lysine (the preceding two residues in the precursor protein), D-tyrosine, L-tyrosine, D-tyrosine-glycine, or L-tyrosine-glycine. In addition, one or more methionine residues in urocortin III, such as those at position 12 and 35 of SEQ ID NO:3, may be replaced with Nle residues. Alternatively, the N-terminus may be extended with D-iodotyrosine, L-iodotyrosine, D-iodotyrosine-glycine, and L-iodotyrosine-glycine and the methionine residues at positions 12 and 35 replaced with Nle. The iodotyrosine residues may be labeled with $^{125}I$.

Additional substitutions are suggested by amino acid residues conserved in other urocortin and urocortin-related proteins which differ in urocortin III. Such urocortin analogs may be comprised of urocortin III with one or more amino acid substitutions selected from the group consisting of $Ile_3$, $Nle_3$, $C_\alpha Me-Leu_3$, $Ile_5$, $Nle_5$, $C_\alpha Me-Leu_5$, $Leu_7$, $Nle_7$, $Thr_8$, $Ile_9$, $Phe_9$, $Gly_{10}$, $His_{10}$, $Leu_{11}$, $Nle_{11}$, $Leu_{12}$, $Nle_{12}$, $Arg_{13}$, $Gln_{13}$, $Nle_{14}$, $C_\alpha Me-Leu_{14}$, $Nle_{15}$, $C_\alpha Me-Leu_{15}$, $Leu_{16}$, $Nle_{16}$, $Glu_{17}$, $Asp_{17}$, $Arg_{20}$, $Nle_{24}$, $C_\alpha Me-Leu_{24}$, $Arg_{32}$, $Ile_{34}$, $Nle_{34}$, $C_\alpha Me-Leu_{34}$, $Leu_{35}$, $Nle_{35}$, $Asp_{36}$, $Glu_{36}$, and $Val_{38}$.

The instant invention is also directed to a CRF-R2 receptor antagonist comprising urocortin III protein or a urocortin III analog wherein the first five to eight N-terminal amino acids of the protein have been deleted. This antagonist may be incorporated into a pharmaceutical composition and used to treat congestive heart failure, vascular disease, gastrointestinal dysfunction and migraine headaches or as an angiogenesis inhibitor.

In yet another embodiment of the instant invention, Urocortin III may also be modified to contain a fluorescent label or a complexing agent for radionuclides. The resulting labeled urocortin III can be used to identify cells expressing urocortin III receptors. Alternatively, urocortin III may be linked to a toxin molecule.

In yet another embodiment of the instant invention, an antibody directed against urocortin III is provided. In a preferred embodiment, the antibody is a monoclonal antibody. The antibody may be conjugated to a molecular label such as a fluorescent label, photoaffinity label or radioactive markers. Alternatively, the antibody could be conjugated to a cytotoxic compound to form an immunotoxin.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the nucleotide and peptide sequences of human urocortin III.

FIG. 2A shows the predicted amino-acid sequence encoding human Ucn III while FIG. 2B shows the amino acid sequence of mouse Ucn III. Amino acids are numbered starting with the initiating methionine. The putative mature peptide coding region is indicated in the boxed area. The complete nucleotide sequences have been deposited with Genbank (accession nos. AF361943 for human Ucn III and AF361944 for mouse Ucn III).

FIG. 3A shows results from A7r5 rat aortic smooth muscle cells. $EC_{50}$: mUcn II: 0.18 nM; mUcn III: 3.7 nM; hUcn III: 80.9 nM. FIG. 3B shows results from primary rat anterior pituitary cells which were established in culture and were stimulated with various peptides for 45 min. $EC_{50}$: rUcn: 2.3 nM; hUcn II: 1 µM*, mUcn II: 0.75 µM* (*: estimated using the plateau of rUcn).

FIGS. 5A-5F show hybridization histochemical localization of Ucn III mRNA in the rat brain. Positive hybridizing signal was most prominent in three regions of the ventral forebrain. These included the median preoptic nucleus (FIGS. 5A, 5B), the rostral perifornical area which encompasses areas just lateral to the paraventricular nucleus (FIG. 5C), and the posterior part of the bed nucleus of stria terminalis (FIG. 5D), and the medial amygdaloid nucleus (FIG. 5E). In the brain stem, positive hybridization signals were detected mainly in the superior paraolivary nucleus (FIG. 5F). Abbreviations: 3V: third ventricle; ac: anterior commissure; BSTp: posterior part of the bed nucleus of stria terminalis; fx: formix; MeA: medial nucleus of amygdala; MePO: median preoptic nucleus; OVLT: vascular organ of the lamina terminalis; opt: optic tract; PVH: paraventricular nucleus of hypothalamus; SPO: superior paraolivary nucleus; Tz: nucleus of the trapezoid body. Scale bars=50 µm.

DETAILED DESCRIPTION OF THE INVENTION

Figure 2C:
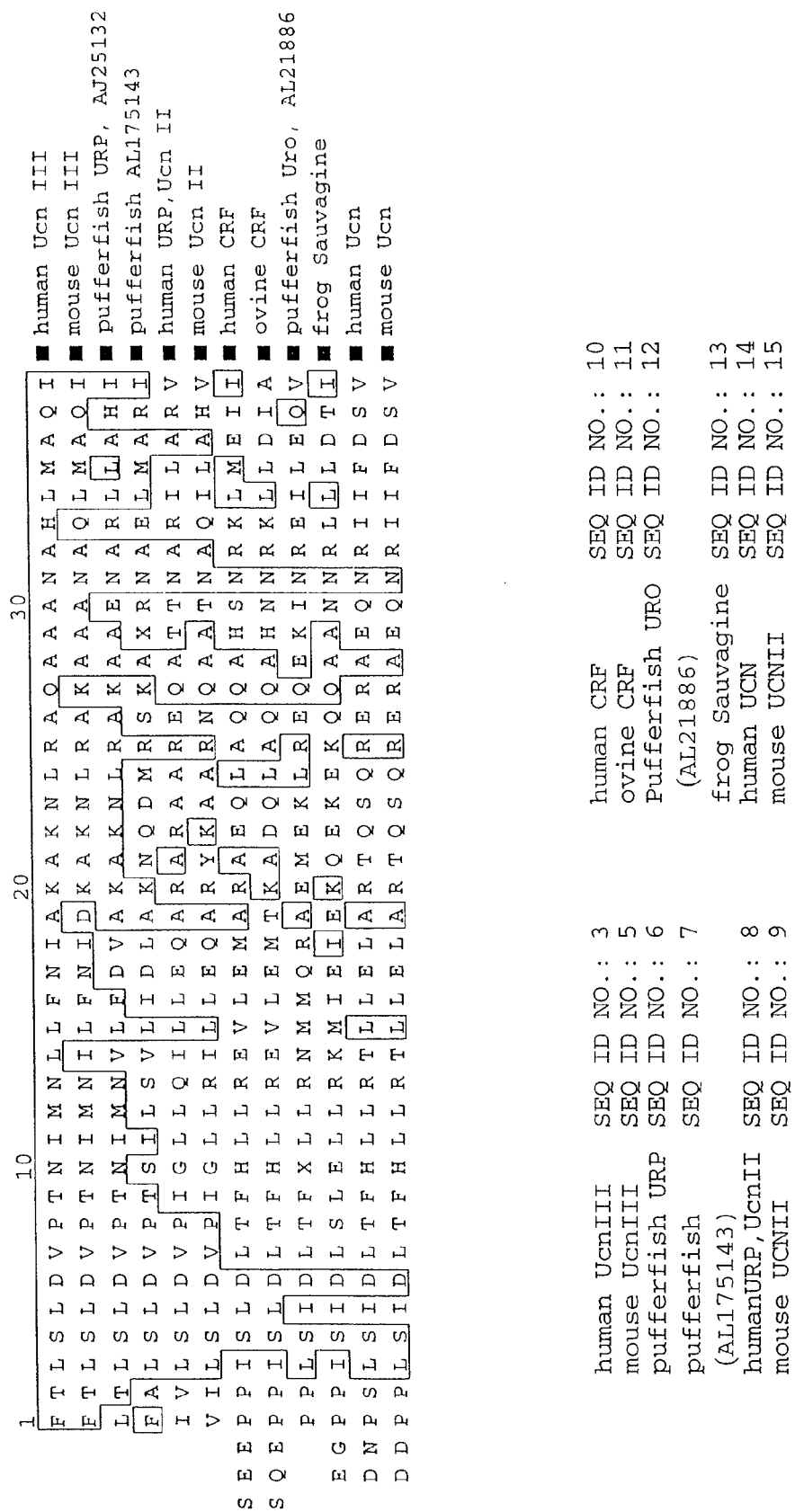
FIG. 2C shows the alignment of putative mature peptide regions of human and mouse Ucn III with homologous pufferfish urocortins, human and mouse Ucn II, human and ovine CRF, pufferfish urotensin (Uro), frog sauvagine, human and mouse Ucn. Residues identical to human Ucn III sequence are boxed. Alignment was made using the Clustal Method of Megalign in DNASTAR. ■, Amidation site (putative for human Ucn II).

In accordance with the present invention there may be employed conventional molecular biology, microbiology, and recombinant DNA techniques, all within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins Eds. (1985)]; "Transcription and Translation" [B. D. Hames & S. J. Higgins Eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Other employed techniques may be peptide synthetic (Stewart, J. M.; Young, J. D. Solid Phase Peptide Synthesis. In *Solid Phase Peptide Synthesis*; Eds.; Pierce Chemical Co.: Rockford, Ill., 1984; V. pp 176), analytical chemistry (Miller, C.; Rivier, J. Peptide chemistry: Development of high-performance liquid chromatography and capillary zone electrophoresis. *Biopolymers* 1996, 40, 265-317.), structure activity relationship approaches (including in vivo and in vitro testing and structural analysis using NMR, CD, X-ray crystallography among others) (Gulyas, J.; Rivier, C.; Perrin, M.; Koerber, S. C.; Sutton, S.; Corrigan, A.; Lahrichi, S. L.; Craig, A. G.; Vale, W. W.; Rivier, J. Potent, structurally constrained agonists and competitive antagonists of corticotropin releasing factor (CRF). *Proc. Natl. Acad. Sci. USA* 1995, 92, 10575-10579).

Therefore, if appearing herein, the following terms shall have the definitions set out below.

As used herein, the term "cDNA" shall refer to the DNA copy of the mRNA transcript of a gene.

As used herein, the term "derived amino acid sequence" shall mean the amino acid sequence determined by reading the triplet sequence of nucleotide bases in the cDNA.

As used herein the term "screening a library" shall refer to the process of using a labeled probe to check whether, under the appropriate conditions, there is a sequence complementary to the probe present in a particular DNA library. In addition, "screening a library" could be performed by PCR.

As used herein, the term "PCR" refers to the polymerase chain reaction that is the subject of U.S. Pat. Nos. 4,683,195 and 4,683,202 to Mullis, as well as other improvements now known in the art.

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues.

The amino acids described herein are preferred to be in the "L" isomeric form. However, residues in the "D" isomeric form can be substituted for any L-amino acid residue, as long as the desired functional property of immunoglobulin binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J Biol. Chem.*, 243:3552-59 (1969), abbreviations for amino acid residues are known in the art.

Nonstandard amino acids may be incorporated into proteins by chemical modification of existing amino acids or by de novo synthesis of a protein/peptide. A Nonstandard amino acid refers to an amino acid that differs in chemical structure from the twenty standard amino acids encoded by the genetic code. Post-translational modification in vivo can also lead to the presence of a nonstandard or amino acid derivative in a protein. The N-terminal $NH_2$ and C-terminal COOH groups of a protein can also be modified, for example, by natural or artificial post-translational modification of a protein.

Proteins/peptides may be modified by amino acids substitutions. Often, some changes result in significant changes in the activity (agonists versus antagonists) and potency/affinity of proteins/peptides while other have little or no effect. Conservative substitutions are least likely to drastically alter the activity of a protein. A "conservative amino acid substitution" refers to replacement of amino acid with a chemically similar amino acid, i.e. replacing nonpolar amino acids with other nonpolar amino acids; substitution of polar amino acids with other polar amino acids, acidic residues with other acidic amino acids, etc. Examples of preferred conservative substitutions are set forth in Table I:

TABLE 1

Conservative Amino Acid Substitutions

| Original Residue | Preferred Conservative Substitutions | Most Preferred Conservative Substitution |
| --- | --- | --- |
| Ala (A) | Val; Leu; Ile | Val |
| Arg (R) | Lys; Gln; Asn | Lys |
| Asn (N) | Gln; His; Lys; Arg, Ser | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala, DAla | Pro |
| His (H) | Asn; Gln; Lys; Arg | Arg |
| Ile (I) | Leu; Val; Met; Ala; Phe; Nle | Leu |
| Leu (L) | Ile; Val; Met; Ala; Phe; Nle | Ile |
| Lys (K) | Arg; Gln; Asn | Arg |
| Met (M) | Leu; Phe; Ile, Nle | Leu |
| Phe (F) | Leu; Val; Ile; Ala | Leu |
| Pro (P) | Gly, Sar | Gly |
| Ser (S) | Thr | Thr |
| Thr (T) | Ser | Ser |
| Trp (W) | Tyr, Nal, Cpa | Tyr |
| Tyr (Y) | Trp; Phe; Thr; Ser, His | Phe |
| Val (V) | Ile; Leu; Met; Phe; Ala; Nle | Leu |

Sar = sarcasine, Nal = naphthylalanine, Cpa = 4-chloro-phenylalanine

"Chemical derivative" refers to a subject polypeptide having one or more residues chemically derivatized by reaction of a functional side group. Such derivatized polypeptides include, for example, those in which free amino groups have been derivatized to form specific salts or derivatized by alkylation and/or acylation, p-toluene sulfonyl groups, carbobenzoxy groups, t-butylocycarbonyl groups, chloroacetyl groups, formyl or acetyl groups among others. Free carboxyl groups may be derivatized to form organic or inorganic salts, methyl and ethyl esters or other types of esters or hydrazides and preferably amides (primary or secondary). Chemical derivatives may include those peptides which contain one or more naturally occurring amino acids derivatives of the twenty standard amino acids. For example, 4-hydroxyproline may be substituted for serine; and ornithine may be substituted for lysine. Peptides embraced by the present invention also include peptides having one or more residue additions and/or deletions relative to the specific peptide whose sequence is shown herein, so long as the modified peptide maintains the requisite biological activity.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence, which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein, encoded by the coding sequence.

A "signal sequence" can be included near the coding sequence. This sequence encodes a signal peptide, N-terminal to the polypeptide, which communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide", as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementary with the sequence or hybridize therewith and thereby form the template for the synthesis of the extension product.

As used herein, the terms "restriction endonucleases" and "restriction enzymes" refer to enzymes, each of which cut double-stranded. DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns or synthetic sequences having codons different than the native gene). Allelic variations or naturally occurring mutational events do not give rise to a heterologous region of DNA as defined herein.

The labels most commonly employed for these studies are radioactive elements, enzymes, chemicals that fluoresce when exposed to ultraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

A particular assay system developed and utilized in the art is known as a receptor assay. In a receptor assay, the material to be assayed is appropriately labeled and then certain cellular test colonies are inoculated with a quantity of both the labeled and non-labeled material after which binding studies are conducted to determine the extent to which the labeled material binds to the cell receptors. In this way, differences in affinity between materials can be ascertained.

As used herein, the term "host" is meant to include not only prokaryotes but also eukaryotes such as yeast, plant and animal cells. A recombinant DNA molecule or gene that encodes a protein of the present invention can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris*, mammalian cells and insect cells.

In general, expression vectors containing promoter sequences that facilitate the efficient transcription of the inserted DNA fragment are used in connection with the host. The expression vector typically contains an origin of replication, promoter(s), terminator(s), as well as specific genes that are capable of providing phenotypic selection in transformed cells. The transformed hosts can be fermented and cultured according to means known in the art to achieve optimal cell growth.

Methods well known to those skilled in the art can be used to construct expression vectors containing appropriate transcriptional and translational control signals. See for example, the techniques described in Sambrook et al., 1989, *Molecular Cloning: A Laboratory Manual* (2nd Ed.), Cold Spring Harbor Press, N.Y. A gene and its transcription control sequences are defined as being "operably linked" if the transcription control sequences effectively control the transcription of the gene. Vectors of the invention include, but are not limited to, plasmid vectors and viral vectors.

In one embodiment of the instant invention, an isolated and purified urocortin III protein is provided. This protein may be either the human or mouse urocortin III protein. The human protein is encoded by DNA partially comprised by a human EST, GenBank accession number AW293249 with significant sequence homology to the pufferfish urocortins.

Another embodiment of the instant invention is directed to a human urocortin III protein encoded by a precursor peptide of SEQ ID NO:2. After post-translational modification, the purified human urocortin III preferably has an amino acid sequence corresponding to SEQ ID NO:3.

The instant invention is also directed to modification of the urocortin III proteins. The N-terminal ends of the urocortin III protens may be modified with various acylating agents such as carboxyl-containing moieties, sulfonyl-containing moieties and isocyanates. Alternatively, the N-terminal end of urocortin III may be chemically crosslinked to a toxin molecule. The N-terminus of urocortin III may also be extended with additional amino acids or peptides such as D-tyrosine, L-tyrosine, D-tyrosine-glycine, or L-tyrosine-glycine. In addition, one or more methionine residues in urocortin III, such as those at position 12 and 35 of SEQ ID NO:3, may be replaced with Nle residues. Alternatively, the N-terminus may be extended with D-iodotyrosine, L-iodotyrosine, D-iodotyrosine-glycine, and L-iodotyrosine-glycine and the methionine residues at positions 12 and 35 replaced with Nle. The iodotyrosine residues may be labeled with $^{125}I$.

In another embodiment of the instant invention, pharmaceutical composition comprising a urocortin III protein is provided as well as a method of treating a pathophysiological state using this pharmaceutical composition. The pharmaceutical composition may be administered, for example, to activate the CRF-R2 receptor in an individual and can thus remedy various pathophysiological states such as high body temperature, appetite dysfunction, congestive heart failure, vascular disease, stress and anxiety.

Another embodiment of the instant invention is directed to modification of a urocortin III protein. The N-terminus of urocortin III may be extended with additional amino acids or peptides such as D-tyrosine, L-tyrosine, D-tyrosine-glycine, or L-tyrosine-glycine. In addition, one or more methionine residues in urocortin III, such as those at position 12 and 35 of SEQ ID NO:3, may be replaced with Ile, Val, Leu or preferably Nle residues. Alternatively, the N-terminus may be extended with D-iodotyrosine, L-iodotyrosine, D-iodotyrosine-glycine, and L-iodotyrosine-glycine and the methionine residues at positions 12 and 35 replaced with Nle. The iodotyrosine residues may be labeled with $^{125}I$.

Additional substitutions are suggested by amino acid residues conserved in other urocortin and urocortin-related proteins which differ in urocortin III. Such urocortin analogs may be comprised of urocortin III with one or more amino acid substitutions selected from the group consisting of $Ile_3$, $Nle_3$, $C_\alpha Me\text{-}Leu_3$, $Ile_5$, $Nle_5$, $C_\alpha Me\text{-}Leu_5$, $Leu_7$, $Nle_7$, $Thr_8$, $Ile_9$, $Phe_9$, $Gly_{10}$, $His_{10}$, $Leu_{11}$, $Nle_{11}$, $Leu_{12}$, $Nle_{12}$, $Arg_{13}$, $Gln_{13}$, $Nle_{14}$, $C_\alpha Me\text{-}Leu_{14}$, $Nle_{15}$, $C_\alpha Me\text{-}Leu_{15}$, $C_\alpha Me\text{-}Leu_{16}$, $Leu_{16}$, $Nle_{16}$, $Glu_{17}$, $Asp_{17}$, $Nle_{18}$, $Leu_{18}$, $Arg_{20}$, $Nle_{24}$, $C_\alpha Me\text{-}Leu_{24}$, $Arg_{32}$, $Ile_{34}$, $Nle_{34}$, $C_\alpha Me\text{-}Leu_{34}$, $Leu_{35}$, $Nle_{35}$, $Asp_{36}$, $Glu_{36}$ and $Val_{38}$.

In yet another embodiment of the instant invention, a CRF-R2 receptor antagonist is provided. This antagonist comprises urocortin III protein or urocortin III analog wherein the first five to eight N-terminal amino acids of the protein have been deleted. This antagonist may be incorporated into a pharmaceutical composition and used to treat congestive heart failure, vascular disease, gastrointestinal dysfunction and migraine headaches or may be used as an angiogenesis inhibitor.

In a further embodiment of the instant invention, Urocortin III is modified to contain a fluorescent label or a complexing agent for radionuclides. The resulting labeled urocortin III can be used to identify cells expressing urocortin III receptors. Alternatively, urocortin III may be linked to a toxin molecule.

In yet another embodiment of the instant invention, an antibody directed against urocortin III is provided. In a preferred embodiment, the antibody is a monoclonal antibody. The antibody may be conjugated to a molecular label such as a fluorescent label, photoaffinity label or radioactive markers.

The following examples are given for the purpose of illustrating various embodiments of the invention and are not meant to limit the present invention in any fashion.

EXAMPLE 1

Identification of Human Urocortin III

The human expressed sequence tag (EST) database of Genbank was searched using a pufferfish (Takifugu rubripes) sequence (Genbank accession number AJ251323) related to urocortin (urocortin related peptide, URP) as a probe. This search identified a human EST, GenBank accession number AW293249 with significant sequence homology to the pufferfish urocortins. Sequence homology comparisons of the novel sequence with human urocortin I and urocortin II revealed that the sequence encoded a novel human urocortin, which was designated urocortin III. The partial human EST contained the precursor sequence and the first 29 amino acids of the mature peptide region. Nested primers for urocortin III were designed based on the partial human EST sequence consisting of the sequences 5'-AAG AGT CCC CAC CGC ACC AAG TTC ACC-3' (SEQ ID NO:6) and 5'-TCC CTC GAC GTC CCC ACC AAC ATC ATG-3' (SEQ ID NO:17). These primers were used along with nested anchored primers to screen a Human GenomeWalker Kit (Clontech) by PCR. Nested PCR was performed for 35 cycles consisting of denaturation at 95° C. for five minutes followed by sequence extension at 66° C. for 12 min. The amplified fragments were subcloned into pCRIITOPO vector (Invitrogen), sequenced and found to encode a full-length mature peptide.

To extend sequence information at the C-terminus, primers were designed based on the partial human EST sequence to screen a human GenomeWalker Kit (Clontech) by PCR. Library pools of human genomic DNA were screened using gene specific and anchored primers in a nested PCR strategy. A full-length human gene encoding a protein for a putative peptide was identified. This protein, named urocortin III (Ucn III), is related to other known CRF family members.

EXAMPLE 2

Identification of Mouse Urocortin III by Hybridization Screening

Based on the full-length human Ucn III sequence, a 144 bp probe was generated, spanning the mature peptide region, to search for a mouse ortholog. The probe was used to screen a mouse genomic λFIXII library (Stratagene) by low stringency hybridization. Hybridization was carried out at 42° C. overnight, in 20% formamide/5×SSC/5×Denhardts/0.5% SDS/5% dextran sulfate. Washes were performed in 1×SSC at 55° C. Purified plaques were subcloned into pBluescript and sequenced. A full-length mouse genomic clone was identified and sequenced. A mouse Ucn III cDNA was isolated from whole brain cDNA by PCR using primers designed from the mouse genomic sequence. PCR was performed at 55° C. for 35 cycles with 2 min extension at 72° C.

EXAMPLE 3

Analysis of the Human and Mouse Ucn III Genes

Both the human and mouse Ucn III genes contain two potential initiation sites for translation. The nucleotide sequence of the human gene encodes a protein deduced to be either 161 or 159 amino acids, depending on the N-terminal methionine used, with preference for the first methionine according to the Netstart 1.0 prediction server (22)(FIG. 2A). The mouse gene encodes a protein deduced to be either a 164 or 162 amino acid precursor also with preference for translation beginning at the first methionine (FIG. 2B). Processing of the precursor molecule to generate the putative 38 amino acid mature peptide is predicted to occur by cleavage at the C-terminal side of Lys 119 for the human gene and following Lys 122 for mouse Ucn III. Thus, Ucn III conforms to the rules for processing at monobasic residues (23), similar to Ucn and murine Ucn II. The C-terminal sequence contains a pair of basic residues, (R-K) for the human and (K-K) for the mouse, immediately preceded by a glycine, presumed to be involved in C-terminal amidation. The predicted mature peptide regions of the human and mouse Ucn III peptides are shown in the boxed regions (FIGS. 2A and 2B). Because the mature peptide regions of human and mouse Ucn III differ by only 4 amino acid residues, they are likely to be orthologous. These sequences have been deposited in the Genbank database [accession nos AF361943 (human Ucn III) and AF361944 (mouse Ucn III)].

EXAMPLE 4

Comparison of Ucn III to Other CRF Family Members

Figure 2D:
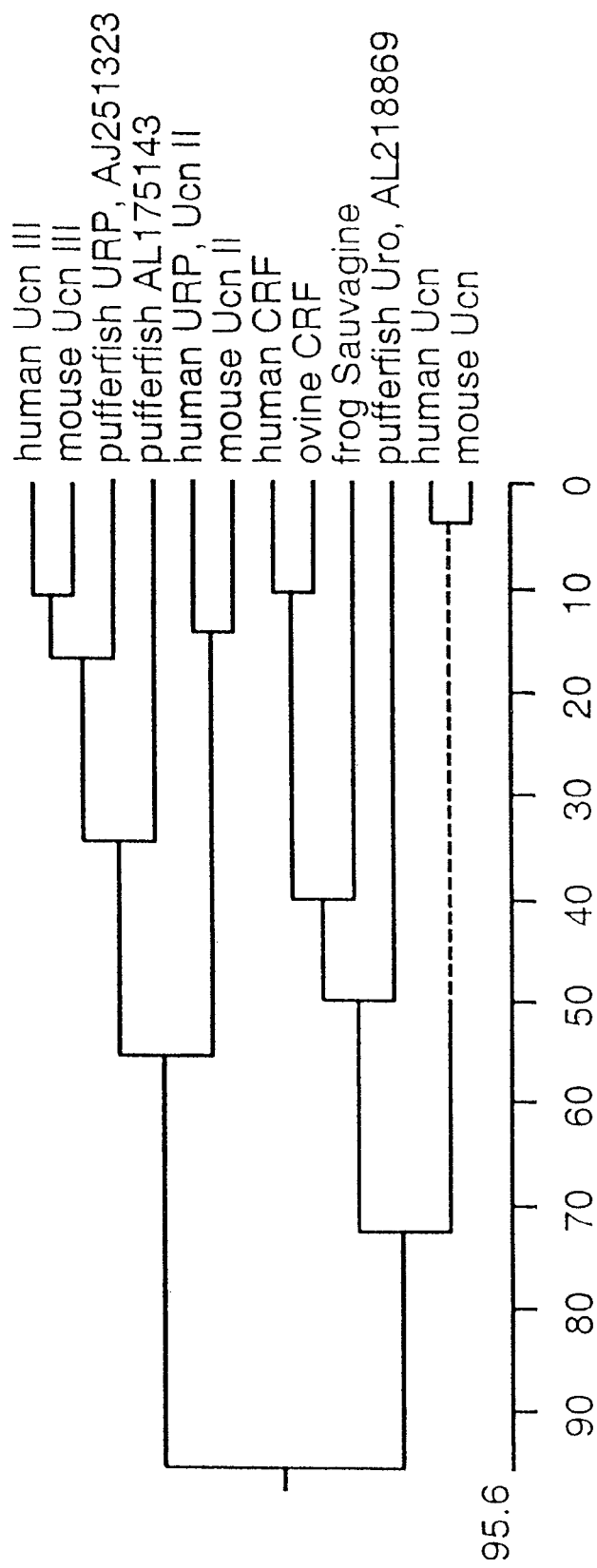
FIG. 2D shows a phylogenetic tree which groups human and mouse Ucn III with the pufferfish urocortins and human and mouse Ucn II. The more distantly related group is comprised of ovine and human CRF, human and mouse Ucn, pufferfish Uro and frog sauvagine. The scale beneath the tree measures sequence distances. The phylogenetic tree was generated by DNASTAR.

In FIG. 2C, the 38 amino acid mature peptide region of human Ucn III sequence is compared to that of other family members. Human and mouse Ucn III share 40% identity to mouse Ucn II. Human and mouse Ucn III share 37% identity to human URP. They are more distantly related to Ucn and CRF. Human and mouse Ucn III share 21% and 18% identity with human and mouse Ucn, respectively. Human and mouse Ucn III share 32% and 26% identity to human/rat CRF. The mammalian urocortins II and III appear to be a separate but related evolutionary branch of the CRF-family with closer ties to two pufferfish urocortins than to mammalian Ucn or CRF (FIG. 2D). Three CRF-family related pufferfish sequences exist to date in the Genbank database. At the amino acid level, the pufferfish urocortin related peptide (URP) (Genbank accession no. AJ251323) is most closely related (76% identity) to both human and mouse Ucn III, and more distantly related to human URP (42%) and mouse Ucn II (37%). A second pufferfish urocortin sequence (Genbank AL175143) is also more closely related to Ucn III (53%) than to any of the other mammalian CRF family members. The third pufferfish peptide (Genbank AL218869) is most similar to the fish urotensin I's with highest amino acid identity to flounder urotensin I (63%).

EXAMPLE 5

Synthesis of Urocortin III

Human and mouse Ucn III were synthesized manually using the solid phase approach, with a 4-methylbenzhydrylamine resin and the Boc-strategy (24). Trifluoroacetic acid (TFA 60% in dichloromethane) was used to remove the Boc groups. Main chain assembly was performed using diisopropylcarbodiimide. The peptide was cleaved and deprotected in hydrofluoric acid and purified using RP-HPLC and three solvent systems (triethylammonium phosphate at pH 2.25 and pH 6.5 and/or 0.1% TFA) (25). Peptides were greater than 95% pure using independent HPLC and capillary zone electrophoresis criteria. Mass spectra confirmed the composition of the preparations.

In addition to the synthesized Urocortin III (calc. Mass 4136.34, found 4136.2) described above, the following synthetic analog were also constructed by the same method: [Tyr-Gly]-Urocortin III (calc Mass 4356.34 found 4356.3); [$Nle_{12,35}$]-Urocortin III (calc. Mass 4100.34 found 4100.2); [$Tyr_0,Nle_{12,35}$]-Urocortin III (calc. Mass 4263.41, found 4263.2) and [$Tyr-Gly_0,Nle_{12,35}$]-Urocortin III (calc. Mass 4320.431, found 4320.4).

EXAMPLE 6

Ucn III Binding Assays

The synthesized urocortin III was assayed for binding to the CRF-R1, CRF-R2α and CRF-R2β receptors by competitive displacement of $^{125}$I[$Tyr^0,Glu^1,Nle^{17}$]sauvagine from Chinese hamster ovary cells stably expressing each receptor type. Stably transfected cell lines expressing CRF-R2α were generously provided by Demitri Grigoriadis, Neurocrine Biosciences Inc. Crude membrane fractions were prepared from Chinese hamster ovary cells stably expressing either cloned human CRF-R1 or mouse CRF-R2β as described (5). Test peptides and radio-ligand, [$^{125}$I$Tyr^0,Glu^1,Nle^{17}$]-sauvagine, diluted in assay buffer (20 mM Hepes/2 mM EGTA/0.1% BSA/10% sucrose, pH 7.6), were combined with membrane fractions (10 μg) in MAGV microtiter plates (Millipore) precoated with 0.1% polyethyleneimine. After 90 min at room temperature, the reaction mixture was filtered and washed twice with assay buffer. The radioligand complex was quantified by gamma-counting. Inhibitory binding constants, $K_i$'s, were determined by GRAPHPAD. The affinities of Ucn II and Ucn III for the CRF binding protein (CRF-BP) were estimated on the basis of the displacement of [$D^{125}$I$Tyr^0$]-hCRF according to the technique described in reference (26).

Data from at least 3 experiments were pooled and inhibitory dissociation constant ($K_i$) values were calculated using the Graphpad Prism program $EC_{50}$ values. The average of their $log_{10}$ value was calculated and used to exponentiate the number 10 to determine an 'average' $EC_{50}$ value. The error was determined by calculating the standard deviation of the $log_{10}$ values, by which the number 10 was exponentiated to determine an error factor. The calculated EC50 was then divided or multiplied by the error factor to determine the lower and upper error bounds, respectively.

Comparisons of the binding affinities and potencies for stimulating cAMP accumulation in cells stably expressing the human CRF-R1, rat CRF-R2α and mouse CRF-R2ß are shown in Table 2. Ucn is significantly more potent than either Ucn II or Ucn III in binding to CRF-R1. Both Ucn II and Ucn III selectively bind both splice variants of CRF-R2, compared to CRF-R1. Human Ucn III displays significantly lower affinity for either type 2 receptor than Ucn or Ucn II. Mouse Ucn III displays considerably higher affinity for murine CRF-R2 receptors than does human Ucn III. Both Ucn II and Ucn III display slightly higher affinities for CRF-R2β compared to CRF-R2α. The potency advantage of mouse Ucn III over human Ucn III is also observed for binding to human CRF-R2α (data not shown).

TABLE 2

Binding Properties and Functional Activities of CRF-family ligands

| Peptide | Binding to Membranes from CHO cells stably expressing hCRF-R1 ($K_i$, nM) | Binding to Membranes from CHO cells stably expressing rCRF-R2α ($K_i$, nM) | Binding to Membranes from CHO cells stably expressing mCRF-R2β ($K_i$, nM) | cAMP in CHO cells stably expressing hCRF-R1 ($EC_{50}$, nM) | cAMP in CHO cells stably expressing rCRF-R2α ($EC_{50}$, nM) | cAMP in CHO cells stably expressing mCRF-R2β ($EC_{50}$, nM) |
|---|---|---|---|---|---|---|
| CRF (rat/human) | 0.53 (0.25-1.15) | 10.1 (6.5-15.6) | 5.2 (1.6-17) | 0.035 (0.014-0.082) | 0.64 (0.03-11.34) | 0.42 (0.17-0.98) |
| Urocortin (rat) | 0.32 (0.14-0.77) | 2.2 (0.91-5.4) | 0.62 (0.14-2.8) | 0.15 (0.03-0.64) | 0.063 (0.014-0.28) | 0.087 (0.017-0.43) |
| Urocortin II (human) | >100 | 1.7 (0.73-4.1) | 0.50 (0.22-1.16) | >100 | 0.26 (0.11-0.61) | 0.42 (0.16-1.1) |
| Urocortin II (mouse) | >100 | 2.1 (0.78-5.4) | 0.66 (0.13-3.3) | >100 | 0.14 (0.04-0.43) | 0.05 (0.02-0.12) |
| Urocortin III (human) | >100 | 21.7 (8.2-57) | 13.5 (9.2-19.7) | >100 | 0.16 (0.09-0.28) | 0.12 (0.06-0.20) |
| Urocortin III (mouse) | >100 | 5.0 (4.0-6.3) | 1.8 (0.77-4.1) | >100 | 0.073 (0.052-0.10) | 0.081 (0.08-0.80) |

The values were determined from three to six independent experiments using stably transfected Chinese hamster ovary cells or their membranes for each test peptide. $EC_{50}$ and $K_i$ values were determined by using PRISM software. Their $log_{10}$ values were averaged (γ). The average $EC_{50}$ or $K_i$ was taken to be $10^γ$. The standard deviation of the $log_{10}$ values was calculated (δ). The ranges given were taken to be [$(10^γ)10^δ$ or $10^γ/10^δ$]. Results are expressed as the average ± sem for three or more independent assays.

EXAMPLE 7

Activation of Adenylate Cyclase in Receptor-Transfected Cells

Chinese hamster ovary cells stably transfected with either human CRF-R1 or murine CRF-R2 were plated into 48-well tissue culture dishes (Costar) and allowed to recover for 24 h. The medium was changed at least 2 h before treatments to DMEM/0.1% FBS. The cells were preincubated with 0.1 mM 3-isobutyl-1-methylxanthine for 30 min and then exposed to peptides for 20 min at 37° C. Intracellular cAMP accumulation in CHO cells stably transfected with either CRF-R1 or CRF-R2 was used as a measure of receptor activation. Both Ucn II and Ucn III have very low potencies to activate CRF-R1 (>100 nM), contrasting sharply with that of Ucn, whose EC50 is 0.15 nM. Indeed, Ucn III shows no activation of CRF-R1 even at very high doses (1 μM). The potencies of Ucn II and III to activate CRF-R2α, and CRF-R2β are approximately equal and nearly equivalent to that of Ucn. Thus, in the cAMP stimulation assay, both Ucn II and III show selectivity for CRF-R2 over CRF-R1, but no preference with respect to CRF-R2α and CRFR-2β. Further, the relative potencies of murine and human Ucn II and Ucn III to functionally activate CRF-R2 overlap in spite of the lower affinity of human Ucn III for binding to CRF-R2.

EXAMPLE 8

Activation of Adenylate Cyclase in Cells Expressing Endogenous Receptors

The abilities of Ucn II and Ucn III to activate adenylate cyclase in cells expressing endogenous CRF-R1 (cultured primary anterior pituitary cells, (5)) or CRF-R2β (A7r5 cells, (27)). Rat aortic smooth muscle cells, A7r5, were plated into 48-well culture dishes and allowed to recover for 48 h. Cells were starved in DMEM/0.2% FBS overnight before the experiment. The cells were preincubated with 0.1 mM 3-isobutyl-1-methylxanthine for 30 min and then exposed to peptides for 20 min at 37° C. Rat anterior pituitary cells were established in culture (28) and treated with test peptides for 45 min at 37° C. Intracellular cAMP was extracted from all cells and measured from triplicate wells using a radioimmunoassay kit (Biomedical Technologies). Potencies were determined using the PRISM GRAPHPAD. The results are shown in FIG. 3.

Figure 3A:
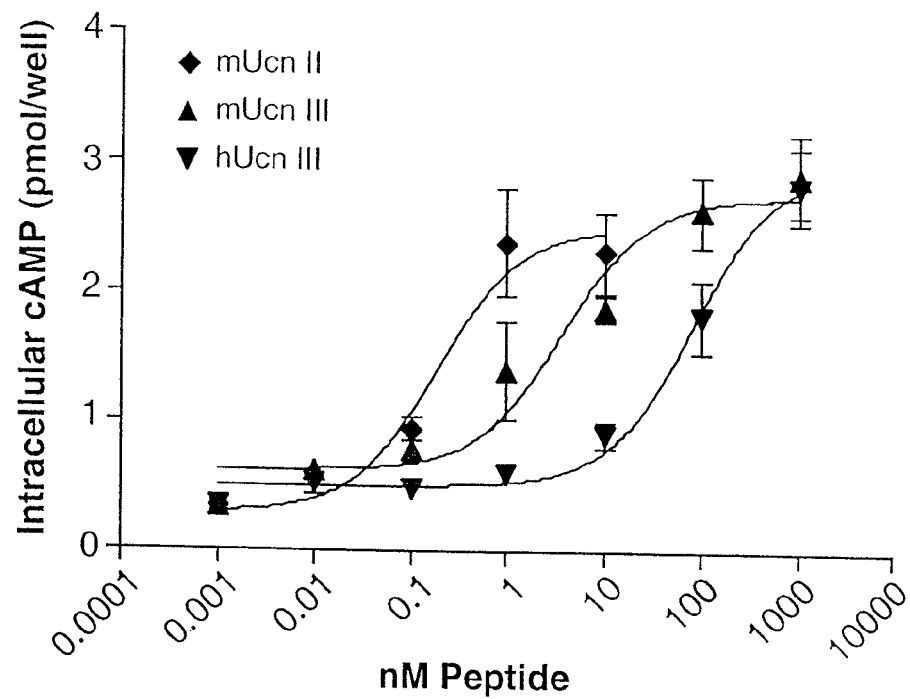
FIGS. 3A and 3B shows the effects of Ucn related peptides on cAMP accumulation in a CRF R2β expressing cell line (FIG. 3A) and primary rat anterior pituitary cells (FIG. 3B).
Figure 3B:
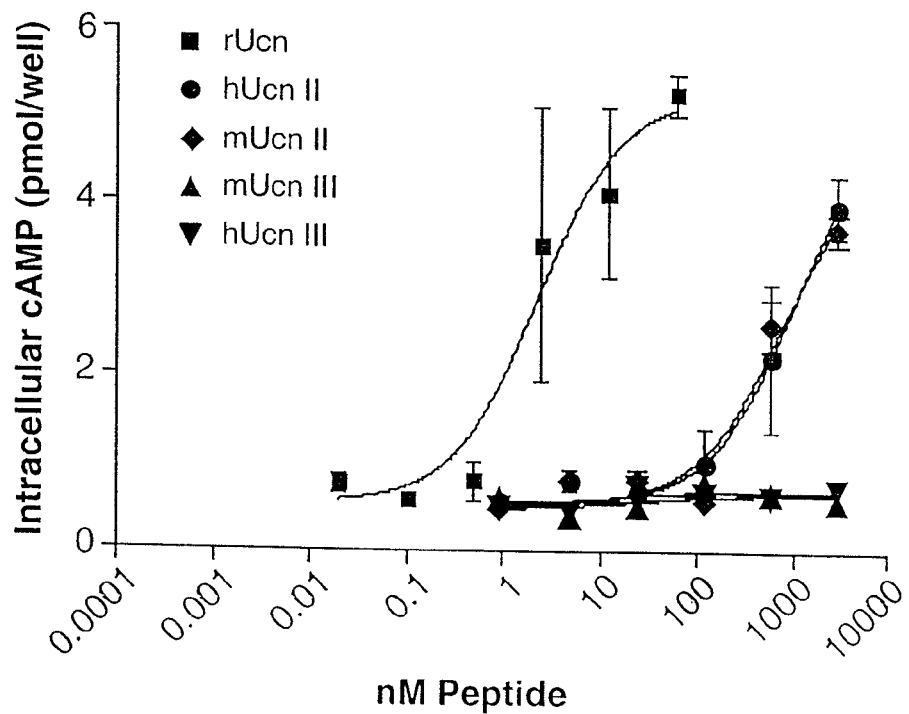

In keeping with the results on transfected receptors, Ucn II and Ucn III are able to activate endogenous CRF-R2β at sub- or low nanomolar concentrations of ligand (FIG. 3A). Expectedly, Ucn II exhibits low potency to increase cyclic AMP in cultured pituitary cells expressing CRF-R1, whereas Ucn III is inactive in this assay even at concentrations >1 μM (FIG. 3B).

EXAMPLE 9

Binding to CRF Binding Protein

As opposed to CRF and urocortin which have subnanomolar affinities for CRF-BP, neither Ucn II nor Ucn III exhibit appreciable affinity for this protein (data not shown). Urocortin III does not have a high affinity for either CRF-R1 or CRF-R2. However, the affinity for CRF-R2 is greater than the affinity for CRF-R1. In view of its high potency to stimulate cyclic AMP production in cells expressing CRF-R2α or β, the affinity is obviously high enough that urocortin III could act as a native agonist of CRF-R2. It is also likely that urocortin III is a stronger agonist of a yet to be identified receptor.

EXAMPLE 10

Ucn III mRNA Expression

RNase protection assays were performed to determine the tissue distribution of mouse Ucn III mRNA. RNase protection analysis was carried out as previously described (29). Total RNA was extracted using TRI REAGENT (Molecular Research Center, Inc., Cincinnati, Ohio). Mouse Ucn III and glyceraldehyde-3-phosphate dehydrogenase (GAPDH) mRNA levels were measured simultaneously by RNase protection, using mouse GAPDH as an internal loading control.

A 528-nucleotide Ucn III antisense riboprobe specific to the mouse Ucn III mRNA was synthesized using T3 RNA polymerase. A 200-nucleotide antisense riboprobe specific to mouse GAPDH mRNA was synthesized using T3 RNA polymerase. All riboprobes were synthesized in the presence of $[\alpha^{-32}P]UTP$ (3,000 Ci/mmol) and either 20 μM UTP for Ucn III or 200 μM UTP for GAPDH, as described (29). The fragments sizes protected by Ucn III and GAPDH riboprobes are 415 and 135 nucleotides, respectively.

RNA samples (50 μg of peripheral tissue or 20-25 μg of brain tissues) were hybridized in 24 μl deionized formamide plus 6 μl hybridization buffer containing 107 cpm of Ucn III and $3\times10^4$ cpm GAPDH antisense riboprobes. After heating to 85° C. for 5 min, the samples were hybridized at 42° C. for 12 h and subsequently digested by RNase (175 μg/ml RNase A and 500 U/ml RNase Ti) at 24° C. for 60 min. The samples were resolved on 5% polyacrylamide urea gels. Image analysis was performed using the PhosphorImager system (Molecular Dynamics, Inc., Sunnyvale, Calif.) and the ImageQuant 4.0 software package.

Figure 4:
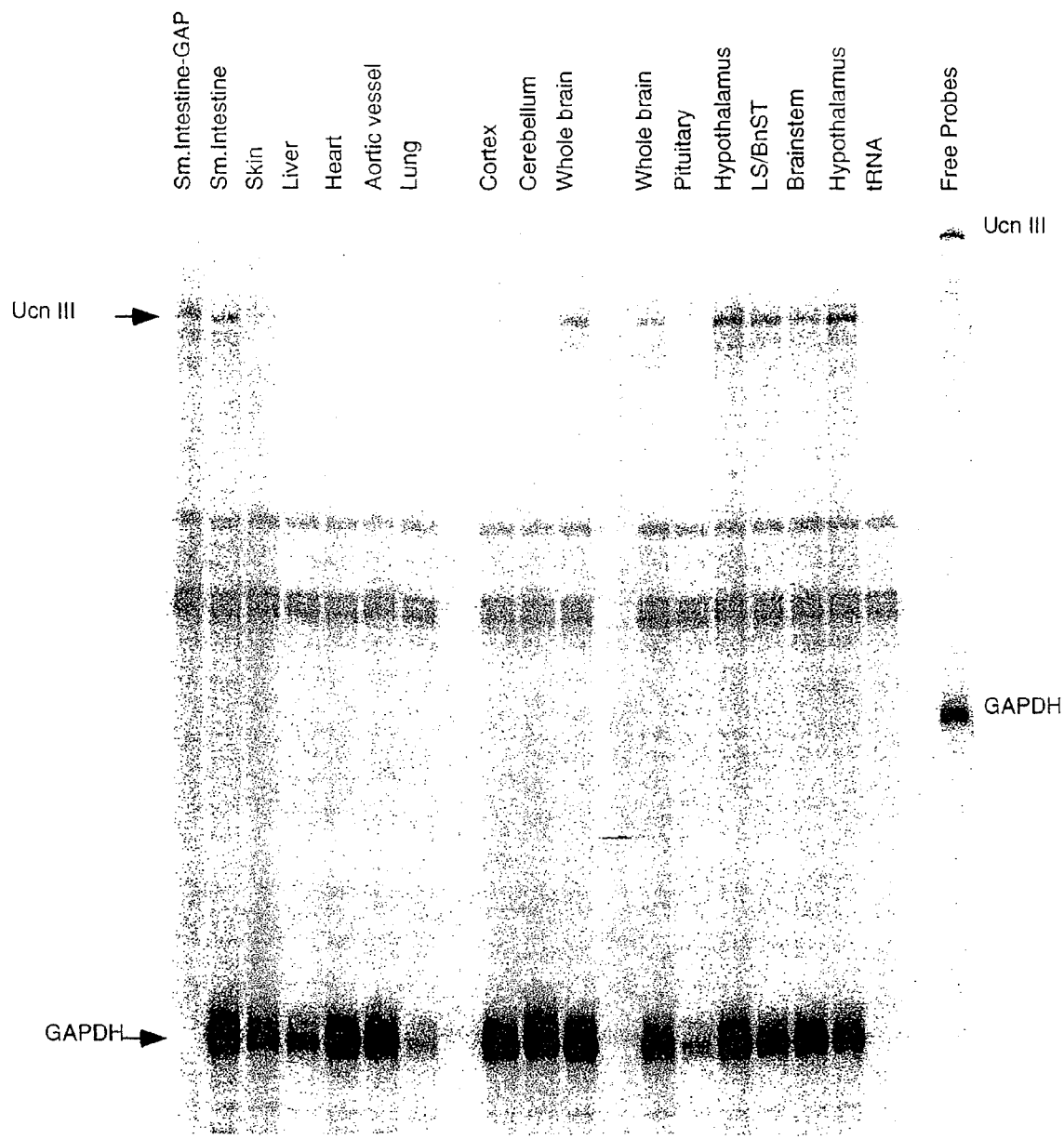
FIG. 4 show the expression of mouse Ucn III mRNA in brain and peripheral tissues. A representative image of RNase protection assay of Ucn III mRNA is shown. Total RNA isolated from each tissue listed was hybridized with the mouse Ucn III antisense probe and mouse GAPDH. The protected fragments were resolved on a 6% polyacrylamide urea gel. Abbreviations: BnST: bed nucleus of stria terminalis.

Total RNA from tissue encompassing several regions of the CNS and peripheral tissues was hybridized with the 528 bp cRNA. This probe spanned the mature peptide region and gave a protected fragment of 415 bp. In the CNS, sites of mRNA expression include the hypothalamus, brainstem, and lateral septum (LS)/bed nucleus of stria terminalis (BnST) (FIG. 4). The pituitary, cerebellum and cerebral cortex showed no detectable mRNA expression. In the periphery, Ucn III mRNA is expressed in small intestine and skin, with no detectable expression in heart, aortic vessel, liver or lung (FIG. 4).

EXAMPLE 11

In Situ Hybridization

To reveal a more detailed pattern of expression of Ucn III in the brain, in situ hybridization was performed on a series of both rat and mouse brain sections using antisense and sense cRNA probes generated from a 415 bp mouse Ucn III cDNA template. Brains and peripheral tissues obtained from adult mice (C57BL/6) and Sprague-Dawley rats were quickly removed and frozen on dry ice. Frozen sections were cut to 20 μm-thick on a cryostat, thaw-mounted onto glass slides, and stored at −80° C. until use. In situ hybridization was performed with $^{33}P$-labeled antisense and sense (control) cRNA probes transcribed from linearized plasmid (pCRIITOPO) containing the mouse Ucn III cDNA (30). Probes were labeled to specific activities of $1-3\times10^9$ dpm/μg, applied to slides at a concentration of about $2.8\times10^7$ cpm/ml and hybridized overnight at 56° C. Slides were washed in SSC of increasing stringency, followed by RNase treatment at 37° C., and finally 0.1×SSC at 65° C. Following dehydration, the slides were exposed to X-ray film (β-Max; Kodak) for 4 days at 4° C. and then coated with Kodak NTB-2 liquid emulsion and exposed at 4° C. for 10 days.

Positive Ucn III mRNA signal was observed only in sections hybridized with the antisense probe. The distribution of Ucn III mRNA expression was found to be limited mainly to a few discrete regions of the ventral forebrain (FIG. 5). One was in the median preoptic nucleus, where a continuous band of positively labeled cells comprised an inverted Y-shaped midline grouping. Neither of the circumventricular cell groups with which the median preoptic nucleus is intimately associated (the vascular organ of the lamina terminalis and the subformical organ) contained positive hybridization signals, and the only additional sites of Ucn III mRNA expression at this level were over scattered cells in medial and lateral preoptic areas. A second major locus of Ucn III mRNA expression appeared as a longitudinally organized cluster of labeled cells associated with (and essentially encircling) the columns of the fornix throughout the rostral hypothalamus.

This cluster includes cells situated within the posterior part of the bed nucleus of the stria terminalis, anterior and lateral hypothalamic areas and the ill-defined region just lateral to (but seldom within) the paraventricular nucleus of the hypothalamus. The caudal extension of this grouping occupied an analagous position, mainly dorsal and lateral to the rostral aspects of the dorsomedial hypothalamic nucleus. Apart from this "rostral periformical" group, scattered positively hybridized neurons were seen reliably in the ventral part of the anterior periventricular nucleus and the retrochiasmatic area. The third major site of Ucn III mRNA expression was over a subset of cells in the anterodorsal part of the medial amygdaloid nucleus. In the brain stem, the only reliable site of Ucn III expression was localized discretely to an auditory-related cell group, the superior paraolivary nucleus (FIG. 5).

EXAMPLE 12

Acylation of Urocortin III

The N-termini of the urocortin III proteins of the instant invention may be extended with acylating agents derived from any of a large number of carboxyl- and sulfonyl-containing moieties including additional amino acids or peptides selected from the group consisting of D-tyrosine, L-tyrosine, D-tyrosine-glycine, and L-tyrosine-glycine. The N-termini of urocortin III protein may also be extended with toxins or isocyanates. Addition of acylating agents may increase resistance to degradation (chemical and enzymatic); modulate the solubility of the protein to allow slow release of therapeutic forms of the proteins; and allowing selective labeling (radioactive, fluorescent, chelators, toxins, photoaffinity, immunospecific, etc).

EXAMPLE 13

Urocortin III Analogs

Previous studies with ligands for other CRF receptors have shown that a number of amino acid substitutions can be made to these ligands without the ligands losing either the ability to bind to appropriate receptors or their bioactivity. A number of previous studies with urocortins have shown that one, two or even three substitutions are tolerated easily. In some instances modifications to urocortin resulted in protein with more desirable pharmacological properties. Since urocortin III is a small protein, such modification can be most easily incorporated by peptide synthesis methods well known to those of skill in the art. These include solid phase techniques, partial solid phase, fragment condensation, and classical solution addition. These methods are especially preferred if nonstandard amino acids are to be incorporated into urocortin III. Alternatively, if the modifications consist entirely of natural amino acids, recombinant DNA techniques can be used for mutagenesis and subsequent expression of modified urocortin III.

Mature urocortin III lacks a tyrosine residue. Since tyrosine residues are useful for the radioiodination of proteins, one possible modification of urocortin III would be to substitute tyrosine for another amino acid in the protein. In previous examples, the addition of a sequence consisting of Tyr-Gly to the N-terminal end of urocortin was described. The resulting protein retains CRF receptor binding and bioactivity but would be useful in the radioiodination of the protein.

Deletion of the first five to eight residues of urocortin was found to result in the formation of effective urocortin antagonists. These proteins were capable of binding to CRF receptors but did not significantly stimulate or activate the receptors. It is expected that deletion of four to eight amino acids from urocortin III would result in effective antagonists as well. It may also be possible to create antagonists of CRF-binding proteins from other urocortin III fragments. These antagonists can be effective in elevating levels of the endogenous peptides, which are normally cleared by CRF-binding protein. By associating with the CRF-binding protein and blocking CRF, urocortin, urocortin II, and urocortin III binding to the same protein, the effective in vivo concentrations of endogenous CRF, Urocortin, Urocortin II and Urocortin III are increased. Such antagonists can be co-administered with other agonists or antagonists of CRF, Urocortin, Urocortin II or Urocortin III for enhancement of the effects thereof.

FIG. 2C shows the results of a homology comparison between urocortin III and equivalent segments of pufferfish urocortin related peptide, mouse urocortin II, human urocortin related peptide, rat urocortin, rat corticotropin releasing factor, ovine corticotropin releasing factor and frog sauvagine. The homology ranges from 20% to 77%. An analysis of FIG. 2C reveals amino acids conserved in other urocortins and urocortin related proteins. While many of the amino acid residues that are conserved in other urocortins and urocortin related proteins are conserved in urocortin III, other amino acid residues differ from those conserved in these other proteins. Therefore, substituting these divergent amino acid residues with those shared by the other urocortin related proteins provides a means by which to design urocortin III analogs for use as agonists and antagonists. For example, while a lysine residue is present at position 20 of urocortin, and arginine residue is present at the analogous position in rat urocortin, mouse urocortin II, human urocortin related peptide and rat corticotropin releasing factor. Therefore, a substitution of $Lys_{20}$ of urocortin with an arginine residue should produce an urocortin III analog which still associates with the CRF receptors but with a modified binding affinity. Other suggested substitutions in urocortin III include $Ile_3$, $Ile_5$, $Leu_7$, $Thr_8$, $Ile_9$, $Phe_9$, $Gly_{10}$, $His_{10}$, $Leu_{11}$, $Leu_{12}$, $Arg_{13}$, $Gln_{13}$, $Leu_{16}$, $Glu_{17}$, $Asp_{17}$, $Arg_{20}$, $Arg_{32}$, $Ile_{34}$, $Leu_{35}$, $Asp_{36}$, $Glu_{36}$ and $Val_{38}$. Since many of these substitutions result in an urocortin III protein closer to the consensus sequence of all urocortin related proteins, it is expected that many of these will bind more strongly to the CRF receptors and thus form potent CRF receptor agonists. Alternatively, by the N-terminal deletion of the first four to eight amino acids as described above, these agonists can be converted into CRF receptor antagonists.

Other possible substitutions include the replacement of the methionine residues at positions 12 and 35 and/or the leucine residues at positions 3, 5, 14, 15, 24 and 34 with Nle or $C_\alpha Me$-$Leu_{15}$ residues. Since comparison of the urocortin III sequence to other urocortin positions suggests the substitution of leucine at positions 7, 11, 12, 16 and 35 or urocortin III, Nle or $C_\alpha Me$-$Leu_{15}$ may be substituted in place of Leu at these positions.

An urocortin III analog containing one or more of the alterations described above is synthesized. Testing in accordance with the general procedure set forth in Example 5 shows improved binding to the CRF-R1, CRF-R2α and/or CRF-R2β receptors by competitive displacement of $^{125}I$ [$Tyr^0,Glu^1,Nle^{17}$]sauvagine from Chinese hamster ovary cells stably expressing each receptor type and alters intracellular cAMP levels. Further testing indicates that the urocortin III analog has beneficial effects in the treatment of high body temperature, appetite dysfunction, congestive heart failure, vascular disease and other cardiovascular conditions, gastrointestinal dysfunction, stress and anxiety, migraine headaches and as a potent inhibitor of angiogenesis.

EXAMPLE 14

Pharmaceutical Administration of Urocortin III and its Analogs

Urocortin III, its analogs or the nontoxic addition salts thereof, combined with a pharmaceutically or veterinarily acceptable carrier to form a pharmaceutical composition, may be administered to mammals, including humans, and other animals either intravenously, subcutaneously, intramuscularly, percutaneously, e.g. intranasally, intrapulmonary, intracerebrospinally, sublingually or orally. The peptides should be at least about 90% pure and preferably should have a purity of at least about 97%; however, lower purities are effective and may well be, used with animals other than humans. This purity means that the intended peptide constitutes the stated weight % of all like peptides and peptide fragments present.

Administration of urocortin III or urocortin III agonists to humans may be employed by a physician to treat high body temperature, appetite dysfunction, congestive heart failure, vascular disease, gastrointestinal dysfunction, stress and anxiety. Urocortin III antagonists may be administered to treat congestive heart failure, vascular disease, gastrointestinal dysfunction and migraine headaches or to inhibit angiogenesis. The required dosage will vary with the particular condition being treated, with the severity of the condition and with the duration of desired treatment. These peptides may also be used to evaluate hypothalamic pituitary adrenal function in animals with suspected endocrine or central nervous system pathology by suitable administration followed by monitoring body functions.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 1 to about 200 micrograms of the peptide per kilogram of the body weight of the host animal.

EXAMPLE 15

Ucn III and Pancreatic Function

Examination of the expression of Ucn III mRNA in the rodents showed that Ucn III is expressed both in the central nervous system and in the periphery. In the periphery, the pancreas and gastrointestinal tract are major organs of Ucn III expression. Further histological studies showed that within the pancreas, Ucn III is co-localized with insulin and, therefore, is in the $\beta$ cells of the Islets of Langerhans.

To determine the function for this new beta cell product, Ucn III given intravenously to rats rapidly stimulated glucagon secretion and subsequently elevates blood sugar levels. It has been shown by others that glucagon can act directly on the beta cell to stimulate insulin secretion in a paracrine manner. Thus, Ucn III may provide a means for the beta cell to signal the alpha cell, which produces glucagon which would then, in turn, drive the beta cell. Thus, Ucn III (or any CRF-R2 agonist) may be used to stimulate and sustain islet functions.

Because insulin and glucagon have opposite effects on blood sugar levels acutely, it is possible that Ucn III might have long term salutary effects on islet functions. On the other hand, given, the possible role of intra-islet Ucn III, it is feasible that a CRF-R2 antagonist might also be useful to reduce production of glucagon, which is a major hyperglycemic factor known to exacerbate diabetic glucose control.

Discussion

Ucn III was identified by sequence homology screening of the human Genbank database. Analyses of the peptide or nucleotide sequences of the complete proteins or putative mature peptide regions of Ucn III and Ucn II suggest that they represent a separate branch of the CRF family more closely related to one another than they are to other members (FIG. 2D). With 76% identity within the putative mature peptide domain, Ucn III and puffer fish URP are likely to be orthologous. In the absence of the identification of any other new urocortin-related peptides, it is likely that the human urocortin-related peptide gene, which is most related to mouse Ucn II, is the human Ucn II ortholog. This suggests that the human URP gene should be renamed human Ucn II. The fact that human Ucn II lacks consensus proteolytic processing residues at the putative C-terminal region (although the potential amide donating glycine is present) raises the possibility that the human Ucn II prohormone may not yield a peptide similar in size to other members of the family. The orthologous relationship between murine and human Ucn II notwithstanding, the chemical nature and functions of urocortin II in the human remain at issue Both mouse and human Ucn III are highly selective for the type 2 CRF receptors and, like Ucn II, exhibit low affinities for type 1 receptors and minimal abilities to induce cyclic AMP production in cells expressing either endogenous (anterior pituitary corticotropes; FIG. 3B) or transfected (Table 2) CRF-R1. Human Ucn III has lower affinity for the type 2 receptors than do either mouse Ucn III or human or mouse Ucn II. Only four residues differ between human and mouse Ucn III providing structure/function insight regarding the requirements for high affinity CRF-R2 binding. Human Ucn III is also less potent on human CRF-R2$\alpha$ (data not shown), indicating that the affinity differences between mouse and human Ucn III are not related to the species source of the receptor. However, in spite of its relatively low binding affinity for CRF-R2, human Ucn III is functionally quite potent (EC50<1 nM) to promote cyclic AMP production by cells expressing this receptor. Therefore, both human and mouse Ucn III exhibit sufficient potency to serve as native ligands for CRF-R2. Neither of the CRF-R2 selective ligands, Ucn III or Ucn II, are bound by CRF-BP with high affinity. By contrast, the two ligands with high affinity for CRF-R1 also have high affinity for CRF-BP.

From the RNase protection analyses, it is feasible that urocortin III could gain access to receptors derived from CRF-R2 in both the brain and periphery. In the periphery, Ucn III mRNA is found in the small intestine and skin, although the cell types in which Ucn III mRNA is expressed remain to be determined. In the GI tract, CRF-R2 has been shown to be involved in modulating gut motility (31).

In the brain, Ucn III mRNA is found in discrete subcortical regions where its distribution is distinct from that of CRF (32), Ucn (33) and Ucn II (21). While identification of the contexts in which Ucn III may operate must await the results of detailed immunohistochemical and functional analyses, some initial insights may be gleaned from its major sites of expression in the median preoptic nucleus, termed here as the rostral perifornical region, and the medial nucleus of the amygdala. By virtue of receiving inputs from both circumventricular structures of the lamina terminalis and the brain stem, the median preoptic nucleus is considered a key site for the integration of neural and humoral signals from the viscera, related to fluid and cardiovascular homeostasis (34) (35). Among the major targets of its projections are multiple relevant neurosecretory and pre-autonomic populations of the paraventricular and/or supraoptic nuclei of the hypothalamus (36), at least some of which are known to express CRF-R2 (37).

It is decidedly more difficult to assign potential functions to the rostral perifornical group of Ucn III-expressing cells, as this cluster spans several cytoarchitectonically defined cell groups, and is distinct from the perifornical hypothalamic nucleus recognized by some authors (38). It may be pointed out, however, that the perifornical region has been identified as a sensitive site of action for several neuroactive agents in stimulating ingestive behavior (39-41), and for excitatory amino acids in eliciting cardiovascular responses (42). Aspects of the perifornical region have been identified as projecting to such major sites of CRF-R2 expression as the lateral septal and ventromedial hypothalamic nuclei (43-45), and the sources of local inhibitory (GABAergic) projections to stress-related neuroendocrine and automomic effectors in the paraventricular nucleus includes a rostral perifornical component (46) whose distribution is very similar to that of Ucn III-expressing neurons.

With regard to the third major site of Ucn III expression identified herein, anatomical and functional studies have indicated that medial nucleus of the amygdala projects extensively to the hypothalamus (including the ventromedial nucleus) and other limbic forebrain structures (47) and is involved in modulation of behaviors (48, 49) and neuroendocrine function (50, 51) related particularly to reproduction and stress. Overall, the central sites of Ucn III expression described here are consistent with potential roles for this peptide in modulating stress-related autonomic, neuroendocrine and behavioral function, perhaps including some previously thought to be a province of other members of this peptide family.

The distributions of each of the three murine urocortins exhibit some potential for interacting with type 2 CRF receptors and each exhibits high affinity for these receptors. By contrast, CRF itself is highly selective for CRF-R1 and has lower affinity for CRF-R2. Under the assumption that the nomenclature for the three urocortin related peptides becomes accepted, it would be reasonable to consider CRF-R2 to be a urocortin receptor both in function and in name. The "CRF system" now includes ligands with selectivity for each receptor type as well as the bivalent ligand, urocortin.

The following references were cited herein:
1. Rivier, C. and W. Vale (1983) *Nature* 305, 325-327.
2. Rivier, J., C. Rivier, and W. Vale (1984) in *European Peptide Symposium*. Djuronaset, Sweden. pp. 104.
3. Vale, et al., (1981) *Science* 213, 1394-1397.
4. Koob, G. F. & Heinrichs, S. C. (1999) *Brain Res.* 848, 141-152.
5. Vaughan, et al., (1995) *Nature* 378, 287-292.
6. Lederis, et al., (1982) *Proc. West. Pharmacol. Soc.* 25, 223-227.
7. Montecucchi, et al., (1980) *Int. J. Pept. Protein Res.* 16, 191-199.
8. Chen, R., et al. (1993) Proc. Natl. Acad. Sci. USA 90, 8967-8971.
9. Perrin et al. (1995) *Proc. Natl. Acad. Sci. USA* 92, 2969-2973.
10. Chen, et al., (1993) in 23rd *Annual Meeting of The Society for Neuroscience*, Washington, D.C., pp. 238.
11. Vita, et al., (1993) *FEBS* 335, 1-5.
12. Chang, et al., (1993) *Neuron* 11, 1187-1195.
13. Perrin, et al., (1993) *Endocrinology* 133, 3058-3061.
14. Kishimoto, et al., (1995) *Proc. Natl. Acad. Sci. USA* 92, 1108-1112.
15. Lovenberg, et al., (1995) *Proc. Natl. Acad. Sci. USA* 92, 836-840.
16. Van Pett, et al., (2000) *J. Comp. Neurol.* 428, 191-212.
17. Potter, E., et al. (1994) in *76th Annual Meeting of The Endocrine Society* Anaheim, Calif. p. 217.
18. Lovenberg, T. W., et al., (1995) *Endocrinology* 136, 3351-3355.
19. Rohde, E., et al. (1996) *Biochem Pharmacol* 52(6), 829-33.
20. Bale, T. L., et al. (1999) *Nat. Genet.* 24(4), 410-414.21.
21. Reyes, et al., (2001) *Proc. Natl. Acad. Sci. USA* 98, 2843-2848.
22. Pedersen, A. G. & Nielsen, H. (1997) *Proc. Int. Conf. Intell. Syst. Mol. Biol.* 5, 226-233.
23. Devi, L. (1991) *Fed. Eur. Biochem. Soc.* 280, 189-194.
24. Miranda, et al., E. (1994) *J. Med. Chem.* 37, 1450-1459.
25. Miller, C. & Rivier, J. (1996) *Biopolymers* 40, 265-317.
26. Sutton, et al., (1995) *Endocrinology* 136, 1097-1102.
27. Kageyama, K., Suda, T. & Vale, W. W. (2001).
28. Vale, et al., (1983) in *Methods in Enzymology: Neuroendocrine Peptides*, ed. Conn, P. M. (Academic Press, New York), Vol. 103, pp. 565-577.
29. Bilezikjian, et al., (1996) *Endocrinology* 137, 4277-4284.
30. Simmons, D. M., Arriza, J. L. & Swanson, L. W. (1989) *J Histotechnol, in press*.
31. Nozu, T., Martinez, V., Rivier, J. & Taché, Y. (1999) *Am. J. Physiol.: Gastrointest. Liver Physiol.* 39, G867-G874.
32. Swanson, et al., (1983) *Neuroendocrinol.* 36, 165-186.
33. Bittencourt, et al., (1999) *J. Comp. Neurol.* 415, 285-312.
34. Johnson, A. K. & Loewy, A. D. (1990) in *Central Regulation of Autonomic Functions*, eds. Loewy, A. D. & Spyer, K. M. (Oxford University Press, New York), pp. 246-267.
35. Saper, C. B. & Levisohn, D. (1983) *Brain Res.* 288, 21-31.
36. Sawchenko, et al., (1983) *J. Comp. Neurol.* 218, 121-144.
37. Chalmers, et al., (1995) *J. Neurosci.* 15, 6340-6350.
38. Paxinos, G. & Watson, C. (1986) Academic Press, San Diego, Calif.
39. Gillard, et al., (1998) *J. Neurosci.* 18, 2646-2652.
40. Stanley, et al., (1993) *Brain Res.* 604, 304-317.
41. Leibowitz, S. F. & Rossakis, C. (1979) *Brain Res.* 172, 101-113.
42. Allen, et al., (1993) *J. Comp. Neurol.* 330, 421-438.
43. Kita, H. & Oomura, Y. (1982) *Brain Res. Bull.* 8, 53-62.
44. Onteniente, B., Menetrey, D., Arai, R. & Calas, A. (1989) *Cell Tissue Res.* 256, 585-592.
45. Szeidemann, et al., (1995) *J. Comp. Neurol.* 358, 573-583.
46. Roland, et al., (1993) *J. Comp. Neurol.* 332, 123-143.
47. Canteras, et al., (1995) *J. Comp. Neurol.* 360, 213-245.
48. Newman, S. W. (1999) *Ann. N.Y. Acad. Sci.* 877, 242-257.
49. Rajendren, G. & Moss, R. L. (1993) *Brain Res.* 617, 81-86.

50. Feldman, et al., (1990) *Neuroscience* 37, 775-779.
51. Dayas, et al., (1999) *Eur. J. Neurosci.* 11, 2312-2322.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. An isolated and purified human urocortin III protein having amino acid sequence SEQ ID NO: 3.

2. The human urocortin III protein of claim 1, wherein the N-terminus of said protein is extended with an acylating agent selected from the group consisting of carboxyl-containing moieties, sulfonyl-containing moieties and isocyanates.

3. The human urocortin III protein of claim 1, wherein the N-terminal end of said protein is extended with additional amino acids or peptides selected from the group consisting of D-tyrosine, L-tyrosine, D-tyrosine-glycine, and L-tyrosine-glycine.

4. The human urocortin III protein of claim 1, wherein the N-terminal end of said protein is chemically crosslinked to a toxin molecule.

5. The human urocortin III protein of claim 1, wherein the N-terminal end of said protein is extended with additional amino acids or peptides selected from the group consisting of D-iodotyrosine, L-iodotyrosine, D-iodotyrosine-glycine, and L-iodotyrosine-glycine and wherein methionine residues at positions 12 and 35 are replaced with Nle.

6. The human urocortin III protein of claim 5, wherein the iodotyrosine residue is labeled with an $^{125}$I radioisotope.

7. The urocortin III protein of claim 1, wherein said protein is SEQ ID NO:3.

8. A pharmaceutical composition comprising the human urocortin protein of claim 1 and a pharmaceutically acceptable carrier.

9. A pharmaceutical composition comprising the human urocortin protein of claim 7 and a pharmaceutically acceptable carrier.

10. A method of treating a pathophysiological state, comprising the step of administering the pharmaceutical composition of claim 8 to an individual in need of such treatment.

11. The method of claim 10, wherein the pathophysiological state is selected from the group consisting of high body temperature, appetite dysfunction, heart disease, vascular disease, stress and anxiety.

12. The method of claim 11, wherein the pathophysiological state is congestive heart failure.

13. A method of treating a pathophysiological state, comprising the step of administering the pharmaceutical composition of claim 9 to an individual in need of such treatment.

14. The method of claim 13, wherein the pathophysiological state is selected from the group consisting of high body temperature, appetite dysfunction, heart disease, vascular disease, stress and anxiety.

* * * * *

UNITED STATES PATENT AND TRADEMARK OFFICE
CERTIFICATE OF CORRECTION

PATENT NO.        : 8,084,413 B2                              Page 1 of 1
APPLICATION NO.   : 12/266430
DATED             : December 27, 2011
INVENTOR(S)       : Wylie W. Vale, Jr. et al.

It is certified that error appears in the above-identified patent and that said Letters Patent is hereby corrected as shown below:

In column 1, lines 22-25, delete paragraph and insert
--This invention was made with government support under grant number P01-DK-26741 awarded by the National Institutes of Health. The government has certain rights in the invention.-- therefor.

Signed and Sealed this
Sixth Day of March, 2012

David J. Kappos
*Director of the United States Patent and Trademark Office*

SEQUENCE LISTING

<160> NUMBER OF SEQ ID NOS: 17

<210> SEQ ID NO 1
<211> LENGTH: 689
<212> TYPE: DNA
<213> ORGANISM: Homo sapiens
<220> FEATURE:
<223> OTHER INFORMATION: DNA encoding human urocortin III

<400> SEQUENCE: 1

```
aattcggcac gagggggacc gtttccatag agagggaata tcacagccca          50
cttaggaaca atacctggag aagcaggagc cgagaccccg gagcagccac         100
aagttcatgg ggacgtgcat ggggccgccc tcctggccct gaagctgcgc         150
cggcctccct gagcgtttcg ctgcggaggg aagtccactc tcggggagag         200
atgctgatgc cggtccactt cctgctgctc ctgctgctgc tcctgggggg         250
ccccaggaca ggcctccccc acaagttcta caaagccaag cccatcttca         300
gctgcctcaa caccgccctg tctgaggctg agaagggcca gtgggaggat         350
gcatccctgc tgagcaagag gagcttccac tacctgcgca gcagagacgc         400
ctcttcggga gaggaggagg agggcaaaga gaaaaagact ttccccatct         450
ctggggccag gggtggagcc ggaggcaccc gttacagata cgtgtcccaa         500
gcacagccca ggggaaagcc acgccaggac acagccaaga gtccccaccg         550
caccaagttc accctgtccc tcgacgtccc caccaacatc atgaacctcc         600
tcttcaacat cgccaaggcc aagaacctgc gtgcccaggc ggccgccaat         650
gcccacctga tggcgcaaat tgggaggaag aagtagagg                      689
```

<210> SEQ ID NO 2
<211> LENGTH: 161
<212> TYPE: PRT
<213> ORGANISM: Homo Sapiens
<220> FEATURE:
<223> OTHER INFORMATION: Human urocortin III Precursor

<400> SEQUENCE: 2

```
Met Leu Met Pro Val His Phe Leu Leu Leu Leu Leu Leu Leu
                 5                  10                  15

Gly Gly Pro Arg Thr Gly Leu Pro His Lys Phe Tyr Lys Ala Lys
                20                  25                  30

Pro Ile Phe Ser Cys Leu Asn Thr Ala Leu Ser Glu Ala Glu Lys
                35                  40                  45

Gly Gln Trp Glu Asp Ala Ser Leu Leu Ser Lys Arg Ser Phe His
                50                  55                  60

Tyr Leu Arg Ser Arg Asp Ala Ser Ser Gly Glu Glu Glu Glu Gly
                65                  70                  75
```

```
Lys Glu Lys Lys Thr Phe Pro Ile Ser Gly Ala Arg Gly Gly Ala
            80                  85                  90

Gly Gly Thr Arg Tyr Arg Tyr Val Ser Gln Ala Gln Pro Arg Gly
            95                  100                 105

Lys Pro Arg Gln Asp Thr Ala Lys Ser Pro His Arg Thr Lys Phe
            110                 115                 120

Thr Leu Ser Leu Asp Val Pro Thr Asn Ile Met Asn Leu Leu Phe
            125                 130                 135

Asn Ile Ala Lys Ala Lys Asn Leu Arg Ala Gln Ala Ala Ala Asn
            140                 145                 150

Ala His Leu Met Ala Gln Ile Gly Arg Lys Lys
            155                 160

<210> SEQ ID NO 3
<211> LENGTH: 38
<212> TYPE: PRT
<213> ORGANISM: Homo Sapiens
<220> FEATURE:
<223> OTHER INFORMATION: Human urocortin III (hUcn III)

<400> SEQUENCE: 3

Phe Thr Leu Ser Leu Asp Val Pro Thr Asn Ile Met Asn Leu Leu
            5                   10                  15

Phe Asn Ile Ala Lys Ala Lys Asn Leu Arg Ala Gln Ala Ala Ala
            20                  25                  30

Asn Ala His Leu Met Ala Gln Ile
            35

<210> SEQ ID NO 4
<211> LENGTH: 164
<212> TYPE: PRT
<213> ORGANISM: Mus musculus
<220> FEATURE:
<223> OTHER INFORMATION: Mouse urocortin III Precursor

<400> SEQUENCE: 4

Met Leu Met Pro Thr Tyr Phe Leu Leu Pro Leu Leu Leu Leu Leu
            5                   10                  15

Gly Gly Pro Arg Thr Ser Leu Ser His Lys Phe Tyr Asn Thr Gly
            20                  25                  30

Pro Val Phe Ser Cys Leu Asn Thr Ala Leu Ser Glu Val Lys Lys
            35                  40                  45

Asn Lys Leu Glu Asp Val Pro Leu Leu Ser Lys Lys Ser Phe Gly
            50                  55                  60

His Leu Pro Thr Gln Asp Pro Ser Gly Glu Glu Asp Asn Gln
            65                  70                  75

Thr His Leu Gln Ile Lys Arg Thr Phe Ser Gly Ala Ala Gly Gly
            80                  85                  90

Asn Gly Ala Gly Ser Thr Arg Tyr Arg Tyr Gln Ser Gln Ala Gln
            95                  100                 105

His Lys Gly Lys Leu Tyr Pro Asp Lys Pro Lys Ser Asp Arg Gly
            110                 115                 120

Thr Lys Phe Thr Leu Ser Leu Asp Val Pro Thr Asn Ile Met Asn
            125                 130                 135

Ile Leu Phe Asn Ile Asp Lys Ala Lys Asn Leu Arg Ala Lys Ala
            140                 145                 150

Ala Ala Asn Ala Gln Leu Met Ala Gln Ile Gly Lys Lys Lys
            155                 160
```

```
<210> SEQ ID NO 5
<211> LENGTH: 38
<212> TYPE: PRT
<213> ORGANISM: Mus musculus
<220> FEATURE:
<223> OTHER INFORMATION: Mouse urocortin III (mUcn III)

<400> SEQUENCE: 5

Phe Thr Leu Ser Leu Asp Val Pro Thr Asn Ile Met Asn Ile Leu
                 5                  10                  15

Phe Asn Ile Asp Lys Ala Lys Asn Leu Arg Ala Lys Ala Ala Ala
                20                  25                  30

Asn Ala Gln Leu Met Ala Gln Ile
                35

<210> SEQ ID NO 6
<211> LENGTH: 38
<212> TYPE: PRT
<213> ORGANISM: Takifugu rubripes
<220> FEATURE:
<223> OTHER INFORMATION: Pufferfish Urocortin Related Peptide
      (pfURP) (AJ25132)

<400> SEQUENCE: 6

Leu Thr Leu Ser Leu Asp Val Pro Thr Asn Ile Met Asn Val Leu
                 5                  10                  15

Phe Asp Val Ala Lys Ala Lys Asn Leu Arg Ala Lys Ala Ala Glu
                20                  25                  30

Asn Ala Arg Leu Leu Ala His Ile
                35

<210> SEQ ID NO 7
<211> LENGTH: 38
<212> TYPE: PRT
<213> ORGANISM: Takifugu rubripes
<220> FEATURE:
<221> NAME/KEY: PEPTIDE
<222> LOCATION: 29
<223> OTHER INFORMATION: Pufferfish (AL175143); Xaa is unknown

<400> SEQUENCE: 7

Phe Ala Leu Ser Leu Asp Val Pro Thr Ser Ile Leu Ser Val Leu
                 5                  10                  15

Ile Asp Leu Ala Lys Asn Gln Asp Met Arg Ser Lys Ala Xaa Arg
                20                  25                  30

Asn Ala Glu Leu Met Ala Arg Ile
                35

<210> SEQ ID NO 8
<211> LENGTH: 38
<212> TYPE: PRT
<213> ORGANISM: Homo sapiens
<220> FEATURE:
<223> OTHER INFORMATION: Human Urocortin-related peptide (hURP),
      human urocortin II

<400> SEQUENCE: 8

Ile Val Leu Ser Leu Asp Val Pro Ile Gly Leu Leu Gln Ile Leu
                 5                  10                  15

Leu Glu Gln Ala Arg Ala Arg Ala Ala Arg Glu Gln Ala Thr Thr
                20                  25                  30

Asn Ala Arg Ile Leu Ala Arg Val
                35
```

-continued

<210> SEQ ID NO 9
<211> LENGTH: 38
<212> TYPE: PRT
<213> ORGANISM: Mus musculus
<220> FEATURE:
<223> OTHER INFORMATION: Mouse Urocortin II (mUcn II)

<400> SEQUENCE: 9

Val Ile Leu Ser Leu Asp Val Pro Ile Gly Leu Leu Arg Ile Leu
                 5                  10                  15

Leu Glu Gln Ala Arg Tyr Lys Ala Ala Arg Asn Gln Ala Ala Thr
             20                  25                  30

Asn Ala Gln Ile Leu Ala His Val
             35

<210> SEQ ID NO 10
<211> LENGTH: 41
<212> TYPE: PRT
<213> ORGANISM: Homo sapiens
<220> FEATURE:
<223> OTHER INFORMATION: Human Corticotropin Releasing Factor (hCRF)

<400> SEQUENCE: 10

Ser Glu Glu Pro Pro Ile Ser Leu Asp Leu Thr Phe His Leu Leu
                 5                  10                  15

Arg Glu Val Leu Glu Met Ala Arg Ala Glu Gln Leu Ala Gln Gln
             20                  25                  30

Ala His Ser Asn Arg Lys Leu Met Glu Ile Ile
             35                  40

<210> SEQ ID NO 11
<211> LENGTH: 41
<212> TYPE: PRT
<213> ORGANISM: Ovis aries
<220> FEATURE:
<223> OTHER INFORMATION: Ovine Corticotropin Releasing Factor (oCRF)

<400> SEQUENCE: 11

Ser Gln Glu Pro Pro Ile Ser Leu Asp Leu Thr Phe His Leu Leu
                 5                  10                  15

Arg Glu Val Leu Glu Met Thr Lys Ala Asp Gln Leu Ala Gln Gln
             20                  25                  30

Ala His Asn Asn Arg Lys Leu Leu Asp Ile Ala
             35                  40

<210> SEQ ID NO 12
<211> LENGTH: 38
<212> TYPE: PRT
<213> ORGANISM: Takifugu rubripes
<220> FEATURE:
<221> NAME/KEY: PEPTIDE
<222> LOCATION: 10
<223> OTHER INFORMATION: Pufferfish Urocortin (AL21886); Xaa is unknown

<400> SEQUENCE: 12

Pro Pro Leu Ser Ile Asp Leu Thr Phe Xaa Leu Leu Arg Asn Met
                 5                  10                  15

Met Gln Arg Ala Glu Met Glu Lys Leu Arg Glu Gln Glu Lys Ile
             20                  25                  30

Asn Arg Glu Ile Leu Glu Gln Val
             35

<210> SEQ ID NO 13

```
<211> LENGTH: 40
<212> TYPE: PRT
<213> ORGANISM: Unknown
<220> FEATURE:
<223> OTHER INFORMATION: Frog Sauvagine (fSvg)

<400> SEQUENCE: 13

Glu Gly Pro Pro Ile Ser Ile Asp Leu Ser Leu Glu Leu Leu Arg
                5                   10                  15

Lys Met Ile Glu Ile Glu Lys Gln Glu Lys Glu Lys Gln Gln Ala
            20                  25                  30

Ala Asn Asn Arg Leu Leu Leu Asp Thr Ile
            35                  40

<210> SEQ ID NO 14
<211> LENGTH: 40
<212> TYPE: PRT
<213> ORGANISM: Homo sapiens
<220> FEATURE:
<223> OTHER INFORMATION: Human Urocortin (hUcn)

<400> SEQUENCE: 14

Asp Asn Pro Ser Leu Ser Ile Asp Leu Thr Phe His Leu Leu Arg
                5                   10                  15

Thr Leu Leu Glu Leu Ala Arg Thr Gln Ser Gln Arg Glu Arg Ala
            20                  25                  30

Glu Gln Asn Arg Ile Ile Phe Asp Ser Val
            35                  40

<210> SEQ ID NO 15
<211> LENGTH: 40
<212> TYPE: PRT
<213> ORGANISM: Mus musculus
<220> FEATURE:
<223> OTHER INFORMATION: Mouse Urocortin (mUcn)

<400> SEQUENCE: 15

Asp Asp Pro Pro Leu Ser Ile Asp Leu Thr Phe His Leu Leu Arg
                5                   10                  15

Thr Leu Leu Glu Leu Ala Arg Thr Gln Ser Gln Arg Glu Arg Ala
            20                  25                  30

Glu Gln Asn Arg Ile Ile Phe Asp Ser Val
            35                  40

<210> SEQ ID NO 16
<211> LENGTH: 27
<212> TYPE: DNA
<213> ORGANISM: artificial sequence
<220> FEATURE:
<223> OTHER INFORMATION: Nested primer based on partial human
      EST sequence

<400> SEQUENCE: 16
aagagtcccc accgcaccaa gttcacc                                        27

<210> SEQ ID NO 17
<211> LENGTH: 27
<212> TYPE: DNA
<213> ORGANISM: artificial sequence
<220> FEATURE:
```

```
<223> OTHER INFORMATION: Nested primer based on partial human
      EST sequence

<400> SEQUENCE: 17
tccctcgacg tccccaccaa catcatg                                            27
```